United States Patent [19]

Wagatsuma et al.

[11] Patent Number: 4,576,938

[45] Date of Patent: Mar. 18, 1986

[54] CEPHALOSPORIN COMPOUND AND PROCESS FOR PREPARING THE SAME

[75] Inventors: Mitsuyoshi Wagatsuma, Urawa; Susumu Hatsuno, Kawaguchi; Totaro Yamaguchi, Urawa; Satoshi Ohshima, Iwatsuki, all of Japan

[73] Assignee: Tanabe Seiyaku Co., Ltd., Osaka, Japan

[21] Appl. No.: 447,809

[22] Filed: Dec. 8, 1982

[30] Foreign Application Priority Data

Dec. 8, 1981 [GB] United Kingdom ............ 8137018
Nov. 2, 1982 [GB] United Kingdom ............ 8231243

[51] Int. Cl.$^4$ .................. A61K 31/545; C07D 501/56
[52] U.S. Cl. ........................................ 514/206; 544/27
[58] Field of Search ................. 424/246; 544/27; 514/206

[56] References Cited

U.S. PATENT DOCUMENTS

| | | | |
|---|---|---|---|
| 4,278,671 | 7/1981 | Ochiai et al. | 544/22 |
| 4,328,225 | 5/1982 | Vignau et al. | 424/246 |
| 4,476,122 | 10/1984 | Heymes et al. | 544/27 |
| 4,489,072 | 12/1984 | Sadaki et al. | 544/27 |

FOREIGN PATENT DOCUMENTS

| | | |
|---|---|---|
| 3248218 | 11/1977 | France . |
| 2385722 | 10/1978 | France . |
| 2408612 | 6/1979 | France . |

OTHER PUBLICATIONS

Chemical Abstracts, 98:125765h, Fliri et al., Apr. 1983.

Primary Examiner—Donald G. Daus
Assistant Examiner—Mary E. Ceperley
Attorney, Agent, or Firm—Birch, Stewart, Kolasch & Birch

[57] ABSTRACT

A cephalosporin compound of the formula:

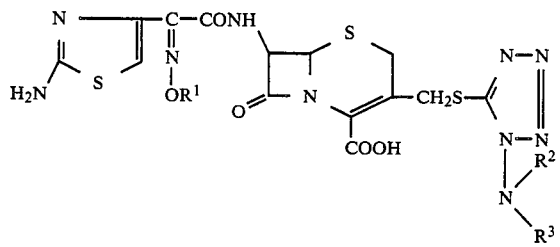

wherein $R^1$ is a hydrogen atom, a lower alkyl group, a carboxy(lower)alkyl group, a hydroxy(lower)alkyl group, a carbamoyl(lower)alkyl group, an N-(lower)alkyl-carbamoyl(lower)alkyl group, a cycloalkyl group, a carboxycycloalkyl group, or a tetrazolylmethyl group, $R^2$ is a hydrogen atom, a lower alkyl group, a formyl group or a lower alkanol group, $R^3$ is a hydrogen atom, or $R^2$ and $R^3$ are combined together to form an aralkylidene group, or a pharmaceutically acceptable salt thereof which is useful as an antimicrobial agent, and process for their preparation.

5 Claims, No Drawings

CEPHALOSPORIN COMPOUND AND PROCESS FOR PREPARING THE SAME

This invention relates to a novel cephalosporin compound and a process for preparing the same. More particularly, it relates to a novel cephalosporin compound of the formula:

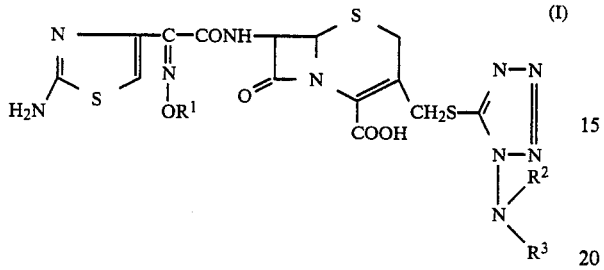

wherein $R^1$ is a hydrogen atom, a lower alkyl group, a carboxy(lower)alkyl group, a hydroxy(lower)alkyl group, a carbamoyl(lower)alkyl group, an N-(lower)alkyl carbamoyl(lower)alkyl group, a cycloalkyl group, a carboxycycloalkyl group or a tetrazolylmethyl group, $R^2$ is a hydrogen atom, a lower alkyl group, a formyl group or a lower alkanoyl group, $R^3$ is a hydrogen atom, or $R^2$ and $R^3$ are combined together to form an aralkylidene group, or a pharmaceutically acceptable salt thereof, a process for preparing the same, and a pharmaceutical composition for use as an antimicrobial agent which comprises the compound (I) or a pharmaceutically acceptable salt thereof as an active ingredient in admixture with a pharmaceutically acceptable carrier or diluent.

According to the present invention, the above-mentioned cephalosporin compound (I) may be prepared for example by condensing a compound of the formula:

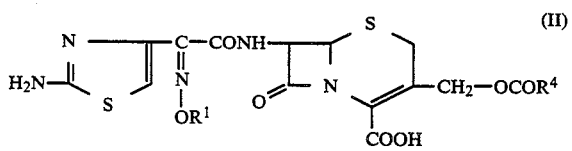

wherein $R^4$ is a lower alkyl group, and $R^1$ is the same as defined above, or a salt thereof with a 5-mercapto-1H-tetrazole compound of the formula:

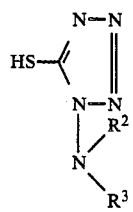

wherein $R^2$ and $R^3$ are the same as defined above, or a salt thereof.

Alternatively, the cephalosporin compound (I) may be prepared for example by the steps of (i) condensing a compound of the formula:

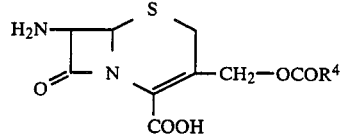

wherein $R^4$ is the same as defined above, or a salt thereof with the 5-mercapto-1H-tetrazole compound (III) to give a compound of the formula:

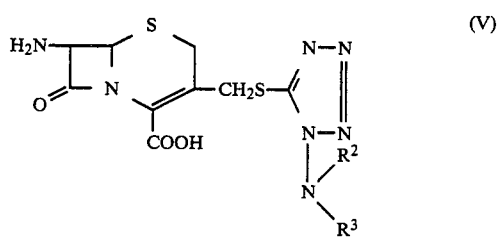

wherein $R^2$ and $R^3$ are the same as defined above, (ii) condensing the compound (V) or a salt thereof with a protected 2-aminothiazole compound of the formula:

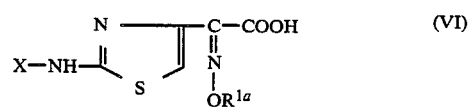

wherein X is a protecting group, and $R^{1a}$ is a protecting group, a lower alkyl group, a protected carboxy(lower)alkyl group, a protected hydroxy(lower)alkyl group, a carbamoyl(lower)alkyl group, an N-(lower)alkyl carbamoyl(lower)alkyl group, a cycloalkyl group or a protected carboxycycloalkyl group, or a reactive derivative thereof at the carboxy group to give a compound of the formula:

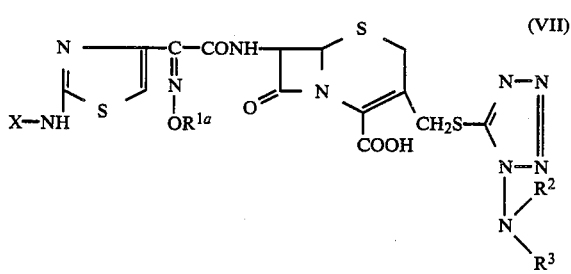

wherein X, $R^{1a}$, $R^2$ and $R^3$ are the same as defined above, and then (iii) removing the protecting groups from the compound (VII).

The terms and definitions described in this specification are illustrated as follows.

Partial structure of the formula:

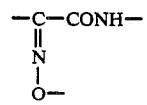

is intended to mean both of the geometric formulae:

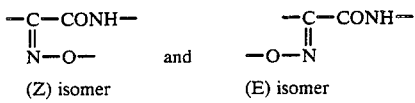

(Z) isomer    (E) isomer

It is considered that the thiazolyl group of the formula:

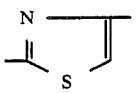

has a thiazolyl-thiazolinyl tautomeric structure represented as follows:

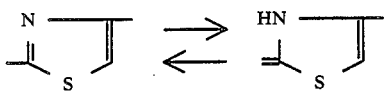

In the present specification, however, said group having the tautomeric structures is represented by using the thiazole structure.

The cephalosporin compound (I) of the present invention in which $R^1$ is tetrazolylmethyl has two isomeric structures: 1H-isomer and 2H-isomer in the tetrazole ring, and these two isomeric structures are mutually converted from one to another. These isomers are both included within the scope of the present invention.

The term "lower" is used to intend a group having 1 to 6 carbon atoms and preferably having 1 to 4 carbon atoms.

The term "protecting" or "protected" in the terms "protecting group", "protected carboxy(lower)alkyl group", "protected carboxy cycloalkyl group" and "protected hydroxy(lower)lower alkyl group" is used to mean that a carboxy, hydroxy or amino group is substituted with a group well known in the β-lactam chemistry as a group used for the protection of a carboxy, hydroxy or amino group.

Suitable protecting groups (X) for an amino group may include acyl (e.g. formyl, monochloroacetyl, trifluoroacetyl, tert-butoxycarbonyl), ar(lower)alkyl (e.g. benzyl, benzhydryl, trityl), tetrahydropyranyl and the like. Suitable protecting groups ($R^{1a}$ or protecting group in protected hydroxy(lower)alkyl) for a hydroxy group may include acyl as aforementioned, tetrahydropyranyl and the like. Suitable protecting groups for carboxy group in protected carboxy(lower)alkyl may include esterified carboxy (e.g. tert-butyl ester, 2-iodoethyl ester, 2,2,2-trichloroethyl ester, benzyl ester).

The term "cycloalkyl" is used to intend a group having 3 to 8 membered cycloalkyl and preferably having 5 or 6 membered cycloalkyl.

The term "aralkylidene" is used to intend an alkylidene group substituted by a substituted or unsubstituted phenyl group wherein the alkylidene group has 1 to 4 carbon atoms, preferably 1 to 2 carbon atoms and the substituent on the phenyl ring includes an alkyl group having 1 to 4 carbon atoms, methoxy and chlorine. Suitable examples of the aralkylidene group are benzylidene and phenylethylidene.

In the process for preparing the compound (I), the condensation reaction of the compound (II) with the compound (III) can be readily effected in the presence of an alkali agent in an aqueous solvent. Preferred examples of said alkali agent include alkali metal bicarbonates (e.g. sodium bicarbonate, potassium bicarbonate), organic amines (e.g. triethylamine) and the like. The aqueous solvent may be for example water, a phosphate buffer solution (pH 6 to 7) or an aqueous hydrophilic organic solvent such as a mixture of said buffer solution and cyanomethane, tetrahydrofuran, methanol, ethanol, dimethylformamide or dioxane. The compound (II) and (III) may be used either in the free form or in the form of a salt. Suitable examples of the salts of said compounds (II) and (III) include alkali metal salts (e.g. sodium salt, potassium salt), organic amine salts (e.g. triethylamine salt) and the like. The reaction is preferably carried out at a temperature between 20° C. and 70° C., especially between 40° C. and 65° C., and in an atmosphere of inert gas.

The condensation reaction of the compound (III) and the compound (IV) can be effected substantially in the same manner as the reaction of the compounds (II) and (III) illustrated above. In a typical embodiment, the reaction is effected in the presence of an alkali agent (e.g. sodium bicarbonate, potassium bicarbonate, triethylamine) in water or in a phosphate buffer solution. In another embodiment, the compound (IV) in the form of a salt is used for the reaction in a phosphate buffer solution. When the compounds (III) and (IV) are used in the free form, the reaction may be conducted in an organic solvent (e.g. cyanomethane, acetic acid, nitromethane), preferably in one having strong polarity. In this case, it is preferred to dissolve the compound (III) in said solvent with the aid of methanesulfonic acid or boron trifluoride etherate prior to the reaction. Suitable examples of the salts of said compounds (III) and (IV) are alkali metal salts (e.g. sodium salt, potassium salt) and organic amine salts (e.g. trimethylamine salt, triethylamine salt). The reaction is preferably carried out at a temperature between 10° C. and 70° C., especially between 20° C. and 50° C., and in an atmosphere of inert gas (e.g. nitrogen gas, argon gas).

The subsequent condensation reaction of the compound (V) with the compound (VI) or the reactive derivative thereof is preferably conducted in a solvent. Suitable examples of the reactive derivative at the carboxy group of the compound (VI) include acid halides (e.g. chloride, bromide), mixed anhydrides (e.g. anhydride with ethoxycarbonic acid, isobutoxycarbonic acid, pivalic acid, trichloroacetic acid, benzoic acid, dibenzylphosphoric acid), activated esters (e.g. benzotriazolyl ester, cyanomethyl ester, nitrophenyl ester, ester with N-hydroxysuccinimide, N-hydroxyphthalimide) and activated amides (e.g. amide with imidazole). If desired, the compound (V) may be used in the form of a salt thereof such as alkali metal salts (e.g. sodium salt, potassium salt), organic amine salts (e.g. trimethylamine salt, triethylamine salt) and the like. Suitable examples of the solvent are dichloromethane, chloroform, tetrahydrofuran, cyanomethane, dimethylformamide, dimethylacetamide, dimethylsulfoxide and a mixture thereof. The reaction is preferably carried out at a temperature between $-30°$ C. and 40° C., especially between $-15°$ C. and $-10°$ C. when the compound (VI) is used in the form of an acid halide or mixed anhydride, and between $-15°$ C. and 10° C. when the compound (VI) is used in the form of an activated ester or amide. Alternatively, the condensation reaction of the compound (V) with the compound (VI) may be conducted by treating the compound (V) with the compound (VI) in the presence of a dehydrating or condensing agent.

Suitable examples of the dehydrating or condensing agent are the N,N'-dicyclohexylcarbodiimide, N,N'-carbonyldiimidazole, N-ethyl-5-phenylisoxazolium-3'-sulfonate, Vilsmeier reagent prepared by the reaction of dimethylformamide with phosphoryl chloride and the like. The reaction is preferably carried out in a solvent such as tetrahydrofuran, cyanomethane, dimethylformamide, dimethylsulfoxide, chloroform or water, at a temperature between −10° C. and 40° C.

Removal of the protecting groups (X, $R^{1a}$) and the protecting groups in the protected carboxy(lower)alkyl group and the protected hydroxy(lower)alkyl group) can be conducted by conventional methods such as hydrolysis, reduction or the like. These methods may be selected according to the kinds of the protecting groups to be removed. For example, when the protecting group is trityl or tetrahydropyranyl, it is preferably removed by treating with formic acid at room temperature. Monochloroacetyl or trifluoroacetyl groups can be removed by treating with thiourea-sodium acetate in tetrahydrofuran or with sodium acetate in water. Formyl groups can be removed by treating with concentrated hydrochloric acid. An ester residue as the carboxy-protecting group such as tert-butyl or trityl can be removed by treating with trifluoroacetic acid. This removal reaction is accelerated by addition of anisole.

Among the starting compounds of the invention, the compound (II) may be obtained, for example, according to the methods described in Tetrahedron 34, 2233 (1978) or Japanese Patent Publication (unexamined) No. 132593/1979. 1-Amino-5-mercapto-1H-tetrazole, i.e., the compound (III) in which both of $R^2$ and $R^3$ are hydrogen atoms, can be obtained by reacting a lower alkyl ester of dithiocarbazic acid with an alkali metal azide at about 50° C. to 85° C. in an alcoholic solvent. On the other hand, the compound (III) in which $R^2$ is formyl or alkanoyl and $R^3$ is a hydrogen atom may be prepared, for example, by formylation or acylation of 1-amino-5-mercapto-1H-tetrazole in a manner known per se. The compound (III) in which $R^2$ and $R^3$ together form an aralkylidene group may be prepared, for example, by reaction of 1-amino-5-mercapto-1H-tetrazole with an aldehyde corresponding to said aralkylidene group, or by reacting a lower alkyl ester of N-aralkylidene-dithiocarbazic acid with tetraalkylguanidinium azide at about 40° C. to 75° C. in an alcoholic solvent in a carbon dioxide gas atmosphere.

The compound (III) in a which $R^2$ is hydrogen atom and $R^3$ is a lower alkyl group, or $R^2$ and $R^3$ are a lower alkyl group may be prepared, for example, by treating 1-acylamino-5-mercapto-1H-tetrazole with a reducing agent (i.e., metalborohydride, alkali metal bis(lower alkoxy-lower alkoxy)aluminum hydride, and the like.); or by the steps of (i) reacting 1-amino-5-mercapto-1H-tetrazole with an aldehyde corresponding to said lower alkyl group to give a N-alkylidene derivative thereof, and (ii) treating the alkylidene derivative with a reducing agent.

The cephalosporin compound (I) of the present invention and a pharmaceutically acceptable salt thereof are novel and useful as antibacterial agents, as nutritional supplements in animal food or as chemotherapeutic agents in poultry and animals, including humans, in the treatment of infectious diseases caused by gram-positive and gram-negative bacteria. That is, said compound (I) and a salt thereof show potent antimicrobial activity against a wide variety of microorganisms, especially against those belonging to the genera Proteus, Pseudomonas and Bacteroides. More specifically, for example, the compound (I) shows the minimum inhibitory concentration (M.I.C) (Agar dilution method, heart infusion agar) of $\geq 0.05$ to 0.1 μg/ml against *Proteus vulgaris*, the M.I.C. of $\geq 0.05$ μg/ml against *Proteus morgani* or *Proteus rettgeri*, the M.I.C. of about 0.78 to 1.56 μg/ml against *Bacteroides fragilis* and the M.I.C. of 1.56 to 3.13 μg/ml against *Pseudomonas aeruginosa*. In addition, the compound (I) in which $R^1$ is methyl or tetrazol-5-yl-methyl and $R^2$ and $R^3$ are hydrogen atoms shows the M.I.C. of 3.13 to 6.25 μg/ml against *Pseudomonas aeruginosa*. The compound (I) and a salt thereof also show potent antimicrobial activity against bacteria belonging to the genera Klebsiella, Clostridium, Enterobacter, Serratia and salmonella. For example, the compound (I) in which $R^1$ is methyl and $R^2$ and $R^3$ are hydrogen atoms shows the M.I.C. of <0.05 μg/ml against *Klebsiella pneumoneae, Enterobacter cloacae* and *Shigella sonnei*, respectively. The compound (I) and a salt thereof further show an anti-microbial activity against strains belonging to the genera Staphylococcus and Escherichia. As for the antimicrobial activity of the compound (I) in which $R^1$ is methyl and $R^2$ and $R^3$ together form a benzylidene group, for example, the M.I.C. of said compound against *Staphylococcus aureus, Staphylococcus epidermidis* and *Streptococcus faecalis* are 1.56, 0.78 and 25 μg/ml, respectively.

The cephalosporin compound (I) and a salt thereof are further characterized in that they have a high stability against a variety of β-lactamases-producing microorganisms, especially against β-lactamases produced by *P. vulgaris* GN 76/C-1 (Ic-type). The toxicity of the cephalosporin compound (I) is low. For example, when the compound (I) in which $R^1$ is methyl or tetrazol-5-ylmethyl and $R^2$ and $R^3$ are hydrogen atom was administered intravenously to mice at a dose of 5 g/kg, no mouse died during the period of 7 days after the administration.

The cephalosporin compound (I) of the present invention can be used for pharmaceutical use either in the free form or in the form of a salt thereof. Pharmaceutically acceptable salts of the compound (I) include, for example, non-toxic metallic salts such as sodium, potassium, calcium or aluminum salts; ammonium salt; salts with non-toxic amines such as trialkylamine (e.g. triethylamine) and procaine; salts with inorganic acids such as hydrochloric acid or hydrobromic acid; salts with organic acids such as oxalic acid or tartaric acid; and so forth. These salts are readily obtained by treating the compound (I) with a stoichiometric amount of the corresponding base or acid, or by salt-interchange. The cephalosporin compound (I) and a salt thereof can be administered either orally or parenterally (e.g. intravenously, intramuscularly, subcutaneously). The daily dose of the compound (I) or a salt thereof may vary over a wide range depending on the age, weight or conditions of patients, and severity of diseases to be treated. In general, however, a preferred daily dose of said compound (I) or a salt thereof may be about 0.5 to about 10 g, especially 0.5 to 4 g, per day. Further, the compound (I) and a salt thereof may be used in the form of a pharmaceutical preparation containing the same compound in conjugation or admixture with pharmaceutical excipients suitable for oral or parenteral administration. Suitable excipients include, for example, gelatin, lactose, glucose, sodium chloride, starch, magnesium stearate, talcum, vegetable oil and other known medicinal excipients. The pharmaceutical preparations may be in solid form such as coated or uncoated tablets, pills, granules or capsules; or in liquid form such as solutions, suspensions or emulsions. They may be sterilized and/or may further contain auxiliaries such as stabilizing, wetting or emulsifying agents.

Practical and presently-preferred embodiments of the present invention are illustratively shown in the following Examples.

EXAMPLE 1

7β-[2-(2-Aminothiazol-4-yl)-(Z)-2-methoxyiminoacetamido]-3-[(1-amino-1H-tetrazol-5-yl)thiomethyl]-3-cephem-4-carboxylic acid sodium salt (a) 1-Amino-5-mercapto-1H-tetrazole 110 g of dithiocarbazic acid methyl ester and 60.4 g of 97% sodium azide were added to a mixture of 2 liters of ethanol and 0.4 liter of water, and the mixture was refluxed for 16 hours. After the reaction, the mixture was evaporated at 40° C. to 45° C. under reduced pressure to remove solvent. 500 ml of ethanol were added to the residue, and the resultant precipitates were collected by filtration. The precipitates were washed with ethanol and then dried, whereby 92 g of 1-amino-5-mercapto-1H-tetrazole sodium salt were obtained as a crude product. 11.22 g of said crude product were dissolved in 40 ml of water. 30 ml of 2N-sulfuric acid were added to said aqueous solution at 0° C. to 5° C., and the mixture was extracted continuously for 3 hours with 270 ml of ether. The extracts were combined and evaporated to remove solvent, and the residue obtained was recrystallized from a mixture of ethyl acetate and n-hexane. 4.3 g of 1-amino-5-mercapto-1H-tetrazole were obtained as colorless needles. mp 162°–163° C. (decomp.)

IR$\nu_{max}^{Nujol}$ (cm$^{-1}$): 3250, 3220, 3050, 1660, 1610

Mass m/e: 117 (M$^+$, base peak), 74, 60, 43, 28

(b) 7β-[2-(2-Aminothiazol-4-yl)-(Z)-2-methoxyiminoacetamido]-3-[(1-amino-1H-tetrazol-5-yl)thiomethyl]-3-cephem-4-carboxylic acid sodium salt 2.05 g of 7β-[2-(2-aminothiazol-4-yl)-(Z)-2-methoxyiminoacetamido]-3-acetoxymethyl-3-cephem-4-carboxylic acid, 0.63 g of 1-amino-5-mercapto-1H-tetrazole and 0.76 g of sodium bicarbonate were dissolved in 60 ml of a phosphate buffer solution (pH 6.4). The solution was stirred at 60° C. for 7.5 hours in an argon gas atmosphere. After the reaction, the solution was freeze-dried. 3.4 g of the yellow powder thus obtained were dissolved in 12 ml of water, and the aqueous solution was passed through the column packed with 200 ml of a styrene-divinylbenzene copolymer (manufactured by Mitsubishi Chemical Industries Ltd., under the trade name "Diaion HP-20"). After the column was washed with water, said column was eluted with 15% aqueous ethanol. Then, the eluates were freeze-dried. 1.70 g of 7β-[2-(2-aminothiazol-4-yl)-(Z)-2-methoxyiminoacetamido]-3-[(1-amino-1H-tetrazol-5-yl)thiomethyl]-3-cephem-4-carboxylic acid sodium salt were thereby obtained as pale yellow powder.

IR$\nu_{max}^{Nujol}$ (cm$^{-1}$): 3300 (broad), 1760, 1660, 1600, 1530

NMR (DMSO-d$_6$)ppm: 3.85 (3H, s, OCH$_3$), 4.33 (2H, s,

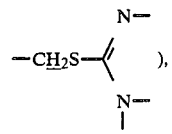

4.95 (1H, d, H at 6th-position), 5.65 (1H, m, H at 7th-position), 6.74 (1H, s, H at 5th-position) of thiazole ring), 6.92 (2H, broad s, —NNH$_2$), 7.23 (2H, broad s, C—NH$_2$), 9.57 (1H, d, —CONH)

EXAMPLE 2

7β1-[2-(2-Aminothiazol-4-yl)-(Z)-2-(tetrazol-5-yl)methoxyimino)acetamido]-3-[(1-amino-1H-tetrazol-5-yl)thiomethyl]-3-cephem-4-carboxylic acid disodium salt 5.23 g of 7β-[2-(2-aminothiazol-4-yl)-(Z)-2-(tetrazol-5-yl)methoxyimino)acetamido]-3-acetoxymethyl-3-cephem-4-carboxylic acid, 1.40 g of 1-amino-5-mercapto-1H-tetrazole and 2.52 g of sodium bicarbonate were dissolved in 150 ml of a phosphate buffer solution (pH 6.4). The solution was stirred at 62° C. for 7 hours. After the reaction, 50 ml of water were added to the solution, and the mixture was freeze-dried. The freeze-dried product was then washed with 50 ml of ethanol and dried, whereby 6.60 g of yellow powder were obtained. 6.60 g of said yellow powder were dissolved in 20 ml of water, and the aqueous solution was passed through the column packed with 600 ml of a styrene-divinylbenzene copolymer (Trade name "Diaion HP-20). After the column was eluted with water, the eluates containing the cephalosporin derivative were combined and freeze-dried. 1.73 g of 7β-[2-(2-aminothiazol-4-yl)-(Z)-2-(tetrazol-5-yl)methoxyimino)acetamido]-3-[(1-amino-1H-tetrazol-5-yl)thiomethyl]-3-cephem-4-carboxylic acid disodium salt were thereby obtained as pale yellow powder.

IR $\nu_{max}^{Nujol}$ (cm$^{-1}$): 3300 (broad), 1750, 1660, 1600, 1530

NMR (DMSO-d$_6$)ppm: 4.35 (2H, s,

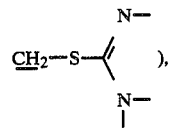

5.00 (1H, d, H at 6th-position), 5.21 (2H, s, =NOCH$_2$—), 5.60 (1H, m, H at 7th-position), 6.70 (1H, s, H at 5th-position of thiazole ring), 6.90 (2H, broad s, N—NH$_2$), 7.35 (2H, broad s, C—NH$_2$), 10.00 (1H, d, —CONH—)

EXAMPLE 3

7β-[2-(2-Aminothiazol-4-yl)-(Z)-2-methoxyiminoacetamido]-3-[(1-formamido-1H-tetrazol-5-yl)thiomethyl]-3-cephem-4-carboxylic acid (a) 1-Formamido-5-mercapto-1H-tetrazole 4.0 g of 1-amino-5-mercapro-1H-tetrazole were suspended in 28 ml of formic acid, and 14 ml of acetic anhydride were added dropwise thereto at 7° to 13° C. under stirring. The mixture was stirred at room temperature for 2.5 hours. The reaction mixture was condensed under reduced pressure, and 5 ml of methanol were added to the residue. The methanol solution obtained was allowed to stand at room temperature for 10 minutes, and then evaporated to remove solvent. Isopropyl ether was added to the residue thus obtained, and crystalline precipitates were collected by filtration. 4.3 g of 1-formamido-5-mercapto-1H-tetrazole are obtained as colorless needles. mp 153° C. (decomp.)

IR $\nu_{max}^{Nujol}$ (cm$^{-1}$): 3200, 1690 (formyl), 1350

Mass m/e: 145 (M$^+$), 117 (M$^+$—N$_2$)

(b)

7β-Amino-3-[(1-formamido-1H-tetrazol-5-yl)thiomethyl]-3-cephem-4-carboxylic acid 2.45 g of 7β-aminocephalosporanic acid and 1.31 g of 1-formamido-5-mercapto-1H-tetrazole were dissolved in 13 ml of acetonitrile, and 4.32 g of methanesulfonic acid were added dropwise thereto at room temperature under stirring. The mixture was stirred at room temperature for 30 minutes and then at 50° C. for 4 hours. 15 ml of water were added to the reaction mixture, and said mixture was adjusted to pH 5 with 28% ammonia. The resultant precipitates were collected by filtration, washed with water and acetone, and then dried. 2.43 g of 7β-amino-3-[(1-formamido-1H-tetrazol-5-yl)thiomethyl]-3-cephem-4-carboxylic acid were obtained as pale yellow powder.

IR $\nu_{max}^{Nujol}$ (cm$^{-1}$): 3180, 1800, 1705, 1620, 1540

NMR (DMSO-d$_6$-CF$_3$COOH)ppm: 3.74 (2H, s, H at 2nd-position), 4.83 (2H, d,

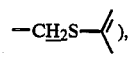

5.15 (2H, s, H at 5th and 6th-position), 8.48 (1H, s, —NHCHO)

Rf: 0.23 (SiO$_2$, acetone-acetic acid=19:1)

(c)

7β-[2-(2-Tritylaminothiazol-4-yl)-(Z)-2-methoxyiminoacetamido]-3-[(1-formamido-1H-tetrazol-5-yl)thiomethyl]-3-cephem-4-carboxylic acid 2.66 g of 2-(2-tritylaminothiazol-4-yl)-(Z)-2-methoxyiminoacetic acid and 3 ml of dimethylacetamide were dissolved in 50 ml of dichloromethane, and a solution of 0.78 ml of oxalyl chloride in 2 ml of dichloromethane was added gradually thereto at −17° to −15° C. under stirring. After the mixture was stirred at the same temperature for 10 minutes, a solution of 3.22 g of 7β-amino-3-[(1-formamido-1H-tetrazol-5-yl)thiomethyl]-3-cephem-4-carboxylic acid and 3.66 g of triethylamine in dichloromethane (40 ml)-dimethylacetamide (30 ml) was added dropwise thereto at −17° to −13° C. for 15 minutes. Then, the mixture was stirred at −18° for 3 hours. After the reaction, the mixture was evaporated under reduced pressure to remove solvent. Water was added to the residue, and the aqueous solution was washed with ethyl acetate, adjusted to pH 3 with citric acid and then extracted twice with a mixture of 20 ml of ethyl acetate and 5 ml of tetrahydrofuran. The extracts were combined, washed with water, dried and evaporated under reduced pressure to remove solvent. Ether was added to the residue thus obtained, whereby 2.87 g of 7β-[2-(2-tritylaminothiazol-4-yl)-(Z)-2-methoxyiminoacetamido]-3-[(1-formamido-1H)-tetrazol-5-yl)thiomethyl]-3-cephem-4-carboxylic acid were obtained as pale brown powder.

IR $\nu_{max}^{Nujol}$ (cm$^{-1}$): 1770, 1710, 1670, 1600, 1520, 1030, 690

Rf: 0.62 (SiO$_2$, n-butanol-water-ethanol-acetic acid=20:4:3:3)

(d)

7β-[2-(2-Aminothiazol-4-yl)-(Z)-2-methoxyiminoacetamido]-3-[(1-foramido-1H-tetrazol-5-yl)thiomethyl]-3-cephem-4-carboxylic acid 2.60 g of 7β-[2-(2-tritylaminothiazol-4-yl)-(Z)-2-methoxyiminoacetamido]-3-[(1-formamido-1H-tetrazol-5-yl)thiomethyl]-3-cephem-4-carboxylic acid were dissolved in 10 ml of 80% formic acid, and the solution was stirred at room temperature for one hour. 40 ml of water were added to the reaction solution, and insoluble materials were removed by filtration. The filtrate was condensed at a temperature below 40° C. under reduced pressure. One ml of tetrahydrofuran and 2 ml of ether were added to the residue, and the resultant precipitates were collected by filtration. 0.72 g of 7β-[2-(2-aminothiazol-4-yl)-(Z)-2-methoxyiminoacetamido]-3-[(1-formamido-1H-tetrazol-5-yl)thiomethyl]-3-cephem-4-carboxylic acid formate thus obtained as pale yellow powder were suspended in 8 ml of ethanol, and the suspension was stirred at 50° C. for 30 minutes. After cooling, the precipitates were collected by filtration. 0.53 g of 7β-[2-(2-aminothiazol-4-yl)-(Z)-2-methoxyiminoacetamido]-3-[(1-formamido-1H-tetrazol-5-yl)thiomethyl]-3cephem-4-carboxylic acid was thereby obtained as pale yellow powder.

NMR (DMSO-d$_6$)ppm: 3.72 (2H, m, CH$_2$ at 2nd-position), 3.88 (3H, s, —OCH$_3$), 4.36 (2H, m,

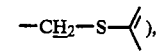

5.19 (1H, d, H at 6th-position), 5.75 (1H, m, H at 7th-position), 6.76 (1H, s, H at 5th-position of thiazole ring), 7.15 (2H, broad s, NH$_2$), 8.52 (1H, s, —NHC$\underline{H}$O), 9.50 (1H, d, —CON$\underline{H}$)

Rf: 0.48 (SiO$_2$, n-butanol-water-ethanol-acetic acid=20:4:3:3)

Sodium salt (dissolved in an aqueous sodium bicarbonate solution and then freeze-dried):

IR $\nu_{max}^{Nujol}$ (cm$^{-1}$): 3320 (broad), 1760, 1670, 1600, 1530

EXAMPLE 4

7β-[2-(2-Aminothiazol-4-yl)-(Z)-2-methoxyiminoacetamido]-3-[(1-benzylideneamino-1H-tetrazol-5-yl)thiomethyl]-3-cephem-4-carboxylic acid sodium salt (a) 1-Benzylideneamino-5-mercapto-1H-tetrazole 7.0 g of 1-amino-5-mercapto-1H-tetrazole and 0.6 g of benzaldehyde were dissolved in 120 ml of ethanol, and the solution was stirred at room temperature for 4 hours. After the reaction, the solution was evaporated to remove solvent. The residue was dissolved in 50 ml of ethyl acetate. The ethyl acetate solution was washed with water, dried and evaporated to remove solvent. Then, isopropyl ether was added to the residue obtained, and the crystalline precipitates were collected by filtration. 8.0 g of 1-benzylideneamino-5-mercapto-1H-tetrazole were obtained as colorless needles. mp 119°-120° C.

IR $\nu_{max}^{Nujol}$ (cm$^{-1}$): 3050, 1630, 1590, 1565

Mass m/e: 205 (M+), 177 (M+—N₂)

(b)

7β-Amino-3-[(1-benzylideneamino-4-1H-tetrazol-5-yl)thiomethyl]-3-cephem-4-carboxylic acid

10.9 g of 7β-aminocephalosporanic acid and 8.2 g of 1-benzylideneamino-5-mercapto-1H-tetrazole were dissolved in 60 ml of acetonitrile, and 19.2 g of methanesulfonic acid were added gradually thereto at a temperature below 30° C. The mixture was stirred at room temperature for 30 minutes and then at 44° C. for 4 hours. After ice-cooling, 400 ml of water were added to the reaction mixture, and said mixture was adjusted to 5.2 with 28% ammonia. The resultant precipitates were collected by filtration, washed with water and tetrahydrofuran, and then dried. 11.53 g of 7β-amino-3-[(1-benzylideneamino-1H-tetrazol-5-yl)thiomethyl]-3-cephem-4-carboxylic acid were obtained as pale yellow powder. mp 170° C. (decomp.)

IR $\nu_{max}^{Nujol}$ (cm⁻¹): 1795, 1625 (shoulder), 1610, 1595, 1570

(c)

7β-[2-(2-Tritylaminothiazol-4-yl)-(Z)-2-methoxyiminoacetamido]-3-[(1-benzylideneamino-1H-tetrazol-5-yl)thiomethyl]-3-cephem-4-carboxylic acid

3.1 g of 2-(2-tritylaminothiazol-4-yl)-(Z)-2-methoxyiminoacetic acid were dissolved in 85 ml of dichloromethane, and 0.61 g of dimethylacetamide was added thereto. A solution of 0.67 ml of oxalyl chloride in 5 ml of dichloromethane was added to the above solution at −32° C. to −10° C. under stirring, and the mixture was stirred at the same temperature for one hour. Then, a solution of 3.4 g of 7β-amino-3-[(1-benzylideneamino-1H-tetrazol-5-yl)thiomethyl]-3-cephem-4-carboxylic acid and 3.4 ml of triethylamine in 35 ml of dichloromethane was added to the mixture at −35° to −28° C., and said mixture was stirred at −35° C. to −10° C. for 2 hours and then at −10° to 0° C. for one hour. The reaction mixture was evaporated under reduced pressure to remove solvent. The residue obtained was dissolved in 50 ml of water, and the aqueous solution was adjusted to about pH 3 with citric acid and extracted twice with 20 ml of ethyl acetate. The extracts were combined, washed with water, dried and then evaporated to remove solvent. 4.81 g of the pale brown powder obtained were purified by dry silica gel column chromatography (silica gel: 100 g), using tetrahydrofuran as an eluant. 3.25 g of 7β-[2-(2-tritylaminothiazol-4-yl)-(Z)-2-methoxyiminoacetamido]-3-[(1-benzylideneamino-1H-tetrazol-5-yl)thiomethyl]-3-cephem-4-carboxylic acid were thereby obtained as pale yellow powder. mp 156°–159° C. (decomp.)

IR $\nu_{max}^{Nujol}$ (cm⁻¹): 1780, 1720 (shoulder), 1680, 1600

NMR (CDCl₃)ppm: 3.71 (2H, broad s, CH₂ at 2nd-position), 4.44 (2H, broad s,

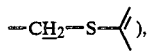

4.90 (3H, s, —OCH₃), 5.06 (1H, d, H at 6th-position), 5.82 (1H, m, H at 7th-position), 6.77 (1H, s, H at 5th-position of thiazole ring), 7.1–8.0 (20H, m, benzene ring proton), 9.13 (1H, s, —N=CH—)

(d)

7β-[2-(2-Aminothiazol-4-yl)-(Z)-2-methoxyiminoacetamido]-3-[(1-benzylideneamino-1H-tetrazol-5-yl)thiomethyl]-3-cephem4-carboxylic acid sodium salt

2.92 g of 7β-[2-(2-tritylaminothiazol-4-yl)-(Z)-2-methoxyiminoacetamido]-3-[(1-benzylideneamino-1H-tetrazol-5-yl)thiomethyl]-3-cephem-4-carboxylic acid were dissolved in 15 ml of 80% formic acid, and the solution was stirred at room temperature for 2 hours. The precipitates were collected by filtration, washed with a mixture of 3 ml of isopropanol and 3 ml of ether, and then dried. 1.61 g of 7β-[2-(2-tritylaminothiazol-4-yl)-(Z)-2-methoxyiminoacetamido]-3-[(1-benzylideneamino-1H-tetrazol-5-yl)thiomethyl]-3-cephem-4-carboxylic acid formate thus obtained were dissolved in 20 ml of tetrahydrofuran. The resultant precipitates were collected by filtration, washed with isopropanol and ether, and then dried. The pale yellow powder thus obtained was dissolved in 15 ml of water. The aqueous solution was passed through the column packed with 50 ml of a styrene-divinylbenzene copolymer (Trade name "Diaion HP-20"). After the column was washed with water, said column was eluted with 20% aqueous ethanol. Then, the eluates obtained were freeze-dried. 1.01 g of 7β-[2-(2-aminothiazol-4-yl)-(Z)-2-methoxyiminoacetamido]-3-[(1-benzylideneamino-1H-tetrazol-5-yl)thiomethyl]-3-cephem-4-carboxylic acid sodium salt were thereby obtained as pale yellow powder.

IR $\nu_{max}^{Nujol}$ (cm⁻¹): 3300 (broad), 1760, 1670, 1600, 1530

NMR (DMSO-d₆)ppm: 3.83 (3H, s, —OCH₃), 4.47 (2H, 2,

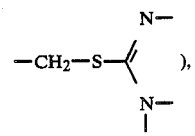

5.0 (1H, d, H at 6th-position), 5.6 (1H, m, m, H at 7th-position), 6.7 (1H, s, H at 5th-position of thiazole ring), 7.1–8.2 (7H, m, NH₂— and benzene ring-protons), 9.35 (1H, s, —CH=N—), 9.5 (1H, d, —CONH—)

Rf: 0.47 (SiO₂, n-butanol-acetic acid-water=4:1:1)

EXAMPLE 5

7β-[2-(2-Aminothiazol-4-yl)-(Z)-2-methoxyiminoacetamido]-3-[(1-benzylideneamino-1H-tetrazol-5-yl)thiomethyl]-3-cephem-4-carboxylic acid

40 g of N-benzylidenedithiocarbazic acid methyl ester and 60 g of tetramethylguanidinium azide were dissolved in 450 ml of isopropanol under heating, and carbon dioxide gas was introduced vigorously into the solution at 70° to 74° C. for 22 hours. After the reaction, the solution was evaporated under reduced pressure to remove solvent. 300 ml of ice-water, 200 ml of ethyl acetate and 40 ml of tetrahydrofuran were added to the residue. The aqueous layer and the organic solvent layer were separated from one to another and said organic solvent layer was extracted with 100 ml of water. The aqueous layer and the aqueous extract were combined, adjusted to pH 3 with citric acid and extracted with a mixture of 200 ml of ethyl acetate and 100 ml of tetrahydrofuran. Said extract was washed with an aqueous saturated sodium chloride solution, dried and then evaporated to remove solvent. A mixture of 30 ml of benzene and 15 ml of isopropyl ether was added to the residue obtained, and the crystalline precipitates were collected by filtration. 16.4 g of 1-benzylideneamino-5-mercapto-1H-tetrazole were obtained as pale yellow crystals. mp 119°–120° C. (decomp.)

1-benzylideneamino-5-mercapto-1H-tetrazole thus obtained was treated in the same manner as described in Example 4-(2) to (4), whereby 7β-[2-(2-aminothiazol-4-yl)-(Z)-2-methoxyiminoacetamido]-3-[(1-benzylideneamino-1H-tetrazol-5-yl)thiomethyl]-3-cephem-4-carboxylic acid sodium salt was obtained.

EXAMPLE 6

7β-[2-(2-Aminothiazol-4-yl)-(Z)-2-methoxyiminoacetamido]-3-[(1-amino-1H-tetrazol-5-yl)thiomethyl]-3-cephem-4-carboxylic acid (a)
7β-Amino-3-[(1-amino-1H-tetrazol-5-yl)thiomethyl]-3-cephem-4-carboxylic acid To a solution of sodium bicarbonate (9.24 g, 0.11 mol) in water (1 liter) was added 7β-aminocephalosporanic acid (27.2 g, 0.1 mol) and the mixture was stirred until solution results. The sodium salt of 1-amino-5-mercapto-1H-tetrazole (27.8 g, 0.2 mol) was added to the mixture and allowed to react in an argon stream between 52° C. and 53° C. for 3 hours. An additional amount of the sodium salt of 1-amino-5-mercapto-1H-tetrazole (6.95 g, 0.5 mol) was added to the mixture and allowed to react at the same temperature for 2 hours. The mixture was then passed three times through a layer of activated carbon (15 g) in order to decolorize it. The filtrate was adjusted to pH 4.6 with methanesulfonic acid (about 6 ml) under ice-cooling and set aside to precipitate. The precipitated substance was filtered, washed with water and dried in vacuo over phosphorus pentoxide to give ocherous powder of 7β-amino-3-[(1-amino-1H-tetrazol-5-yl)thiomethyl]-3-cephem-4-carboxylic acid (17.3 g, 52%), mp~206° C. (decomposition).

IR $\nu_{max}^{Nujol}$ (cm$^{-1}$): 3300, 3150, 1785, 1610, 1520, 1400, 1340, 1280, 1210

NMR(DMSO-d$_6$-CF$_3$COOH)ppm: 3.80 (2H, s, CH$_2$ at 2nd position), 4.40 (2H, dd, J=5.4 and 13.5 Hz, CH$_2$ at C$^{3'}$), 5.20 (2H, s, H at 6th and 7th positions)

(b) 1-Benzotriazolyl 2-(2-tritylaminothiazol-4-yl)-(Z)-2-methoxyiminoacetate

To a solution of 2-(2-tritylaminothiazol-4-yl)-(Z)-2-methoxyiminoacetic acid (2.22 g, 5 mmol) and 1-hydroxybenzotriazole (0.74 g, 5.5 mmol) in tetrahydrofuran (22 ml) was added N,N'-dicyclohexylcarbodiimide (1.14 g, 5.5 mmol) at 5°–10° C. and the mixture was stirred at the same temperature for 3 hours. Precipitated N,N'-dicyclohexylurea was removed by filtration and the filtrate was concentrated under reduced pressure. The residue was dissolved in chloroform (20 ml) and insoluble material was removed by filtration. The chloroform was evaporated and the residue was treated with a small quantity of ether to give colorless needles of 1-benzotriazolyl 2-(2-tritylaminothiazol-4-yl)-(Z)-2-methoxyiminoacetate (2.60 g, 93%), mp 178°–179° C. (decomposition).

IR $\nu_{max}^{Nujol}$ (cm$^{-1}$): 3280, 1815, 1000, 740, 700
Rf: 0.79 (SiO$_2$, n-hexane:ethyl acetate=1:1)

(c)
7β-[2-(2-tritylaminothiazol-4-yl)-(Z)-2-methoxyiminoacetomido]-3-[(1-amino-1H-tetrazol-5-yl)thiomethyl]-3-cephem-4-carboxylic acid To a solution of triethylamine (7.02 g, 69.4 mmol) and water (2.2 ml) in dimethylacetamide (72 ml) was added 7β-amino-3-[(1-amino-1H-tetrazol-5-yl)thiomethyl]-3-cephem-4-carboxylic acid (11.5 g, 34.7 mmol) at room temperature and the mixture was stirred to dissolve it. The mixture was cooled to −6° to −3° C. and a solution of 1-benzotriazolyl 2-(2-tritylaminothiazol-4-yl)-(Z)-2-methoxyiminoacetate (29.2 g, 52.1 mmol) in dimethylacetamide (120 ml) was added dropwise to the mixture and allowed to react at 5° C. for 17 hours. The reaction mixture was poured into ice-water (500 ml). The aqueous layer was washed with ethyl acetate (100 ml)—tetrahydrofuran (50 ml) and adjusted to pH 3 with 20% aqueous sulfuric acid. Precipitated material was extracted with ethyl acetate (200 ml)—tetrahydrofuran (100 ml). The organic layer was filtered to remove insoluble material, washed with water, dried over magnesium sulfate and evaporated under reduced pressure. The residue was treated with ether to give pale yellow substance of 7β-[2-(2-tritylaminothiazol-4-yl)-(Z)-2-methoxyiminoacetamido]-3-[(1-amino-1H-tetrazol-5-yl)thiomethyl]-3-cephem-4-carboxylic acid (15.1 g, 57.7%), mp~175° C. (decomposition).

IR $\nu_{max}^{Nujol}$ (cm$^{-1}$): 3250 (w), 1775, 1670, 1520
NMR(DMSO-d$_6$)ppm: 3.67 (2H, broad s, CH$_2$ at 2nd position), 3.82 (3H, s, OCH$_3$), 4.30 (2H, d, J=6 Hz, CH$_2$ at C$^{3'}$), 5.07 (1H, d, J=4.8 Hz, H at 6th position), 5.70 (1H, m, H at 7th position), 6.73 (1H, s, H at 5th position of thiazole), 6.92 (2H, broad s, N—NH$_2$), 7.34 (15H, s, benzene ring protons), 8.73 (1H, broad s, C—NH), 9.47 (1H, d, J=7.8 Hz, —CONH—)

(d)
7β-[2-(2-aminothiazol-4-yl)-(Z)-2-methoxyiminoacetamido]-3-[(1-amino-1H-tetrazol-5-yl)thiomethyl]-3-cephem-4-carboxylic acid To 80% formic acid (17 ml) was added 7β-[2-(2-tritylaminothiazol-4-yl)-(Z)-2-methoxyiminoacetamido]-3-[(1-amino-1H-tetrazol-5-yl)thiomethyl]-3-cephem-4-carboxylic acid (4.3 g, 5.7 mmol) with stirring at room temperature and the mixture was stirred for an hour and a quarter. After adding water (85 ml), the mixture was filtered to remove insoluble material and the filtrate was concentrated below 45° C. The residue was treated with tetrahydrofuran (10 ml)-ether (5 ml) and concentrated again under reduced pressure. The residue was treated with ether to give pale yellow substances of 7β-[2-(2-aminothiazol-4-yl)-(Z)-2-methoxyiminoacetamido]-3-[(1-amino-1H-tetrazol-5-yl)thiomethyl]-3-cephem-4-carboxylic acid formate (2.98 g, 93.9%).

The formate was suspended in ethanol (15 ml). The suspension was stirred at 50° C. for 40 minutes and allowed to stand under ice-cooling to give pale yellow powder of 7β-[2-(2-aminothiazol-4-yl)-(Z)-2-methoxyiminoacetamido]-3-[(1-amino-1H-tetrazol-5-yl)thiomethyl]-3-cephem-4-carboxylic acid (1.96 g).

The acid thus obtained was dissolved in a solution of sodium bicarbonate (0.32 g) in water (37 ml). The solution was passed through a layer of activated carbon (1.0 g) and lyophilized to give pale yellow powder of the sodium salt (1.51 g, 49.6%).

IR $v_{max}^{Nujol}$ (cm$^{-1}$): 3300 (broad), 1760, 1660, 1600 1530

NMR (DMSO-d$_6$) ppm: 3.85 (3H, S, OCH$_3$), 4.33 (2H, S,

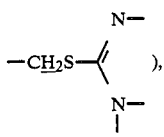), 4.95 (1H, d, H at 6th-position), 5.65 (1H, m, H at 7th-position), 6.74 (1H, S, H at 5th-position of thiazole), 6.92 (2H, broad S, —NNH$_2$), 7.23 (2H, broad S, C—HN$_2$), 9.57 (1H, d, —CONH)

EXAMPLE 7

7β-[2-(2-Aminothiazol-4-yl)-(Z)-2-(2-carboxy-2-propyloxyimino)acetamido]-3-[(1-amino-1H-tetrazol-5-yl)thiomethyl]-3-cephem-4-carboxylic acid To a phosphate buffer (pH 6.4, 15 ml) were added sodium bicarbonate (0.252 g, 3 mmol), 7β-[2-(2-aminothiazol-4-yl)-(Z)-2-(2-carboxy-2-propyloxyimino)acetamido]-3-acetoxymethyl-4-carboxylic acid (0.527 g, 1 mmol) (cf. Eur. J. Med. Chem., 1981, 16, 307) and 1-amino-5-mercapto-1H-tetrazole (0.140 g, 1.2 mmol). The mixture was stirred at 60° C. in an argon stream for 6.5 hours and lyophilized to give pale yellow powder (0.900 g), which was dissolved in water (2 ml) and subjected to column chromatography using styrene-divinylbenzene copolymer (90 ml, manufactured by Mitsubishi Chemical Industries Ltd., under the tradename of "Diaion HP-20"). Elution was effected with water and a fraction containing the desired compound was lyophilized to give pale yellow powder of 7β-[2-(2-aminothiazol-4-yl)-(Z)-2-(2-carboxy-2-propyloxyimino)acetamido]-3-[(1-amino-1H-tetrazol-5-yl)thiomethyl]-3-cephem-4-carboxylic acid disodium salt (0.207 g, 33%).

IR $v_{max}^{Nujol}$ (cm$^{-1}$): 3300, 1755, 1660, 1580, 1400

NMR(DMSO-d$_6$) ppm: 1.40 (3H, s, —CH$_3$), 1.45 (3H, s, —CH$_3$), 3.40 (2H, m, CH$_2$ at 2nd position), 4.35 (2H, m, CH$_2$ at C$^{3'}$), 5.00 (1H, d, J=5 Hz, H at 6th position), 5.70 (1H, m, H at 7th position), 6.70 (1H, s, H at 5th position of thiazole), 6.90 (2H, m, —NH$_2$), 7.20 (2H, m, —NH$_2$), 11.10 (1H, d, J=8 Hz, —CONH—)

EXAMPLE 8

7β-[2-(2-Aminothiazol-4-yl)-(Z)-2-methoxyiminoacetamido]-3-[(1-acetamido-1H-tetrazol-5-yl)thiomethyl]-3-cephem-4-carboxylic acid (a) 1-Acetamido-5-mercapto-1H-tetrazole 1-Amino-5-mercapto-1H-tetrazole (4.18 g) was dissolved in tetrahydrofuran (30 ml), and acetic anhydride (4.01 g) was added thereto. The mixture was refluxed for 6 hours and then condensed under reduced pressure to remove solvent. Methanol (4 ml) was added to the residue thus obtained, and the methanol solution was allowed to stand at room temperature for 20 minutes. The mixture was evaporated to remove solvent. Hot isopropanol was added to the residue thus obtained, and the solution was allowed to stand at room temperature. Crystalline precipitates were collected by filtration. 4.71 g of 1-acetamido-5-mercapto-1H-tetrazole were obtained as colorless needles. mp 147°–148° C. (decomp.)

IR $v_{max}^{Nujol}$ (cm$^{-1}$): 3160, 1695, 1495, 1355, 1250, 1200

Mass m/e: 159 (M$^+$), 116 (M$^+$—COCH$_3$), 99

(b) 7β-Amino-3-[(1-acetamido-1H-tetrazol-5-yl)thiomethyl]-3-cephem-4-carboxylic acid Methanesulfonic acid (5.77 g, 60 mmol) was added dropwise to a solution of 7β-aminocephalosporanic acid (3.27 g, 12.0 mmol) and 1-acetamido-5-mercapto-1H-tetrazole (2.50 g, 15.7 mmol) in acetonitrile (15 ml). The mixture was stirred at room temperature for 30 minutes and at 50° C. for 4 hours. Water (20 ml) was added with cooling to the reaction mixture, which was then adjusted to pH 3.5 with 28% aqueous ammonium hydroxide. Precipitates formed were filtered, washed with water and acetone successively and dried to give pale brown powder of 7β-amino-3-[(1-acetamido-1H-tetrazol-5-yl)thiomethyl]-3-cephem-4-carboxylic acid (3.36 g, 75. 3%), mp~195° C. (decomposition).

IR $v_{max}^{Nujol}$ (cm$^{-1}$): 3170, 1795, 1720, 1610, 1520

NMR(DMSO-d$_6$-CF$_3$COOH)ppm: 2.14 (3H, s, —COCH$_3$), 3.75 (2H, s, CH$_2$ at 2nd position), 4.43 (2H, q, CH$_2$ at C$^{3'}$), 5.16 (2H, s, H at 6th and 7th positions)

(c) 7β-[2-(2-Tritylaminothiazol-4-yl)-(Z)-2-methoxyiminoacetamido]-3-[(1-acetamido-1H-tetrazol-5-yl)thiomethyl]-3-cephem-4-carboxylic acid A mixture of 7β-amino-3-[(1-acetamido-1H-tetrazol-5-yl)thiomethyl]-3-cephem-4-carboxylic acid (0.450 g, 1.21 mmol), triethylamine (0.245 mg, 2.42 mmol) and dichloromethane (10 ml) was stirred at room temperature for 10 minutes. To the mixture was added 1-benzotriazolyl 2-(2-tritylaminothiazol-4-yl)-(Z)-2-methoxyiminoacetate (0.678 g, 1.21 mmol) and allowed to react at 5° C. for 17 hours. The dichloromethane was removed by evaporation. Water (10 ml) and triethylamine (0.5 ml) were added to the residue. The aqueous layer was separated, washed with ethyl acetate (5 ml) and adjusted to pH 3.5 with citric acid. Precipitated substance was extracted with ethyl acetate. The extract was washed with water, dried over magnesium sulfate and concentrated. The residue was treated with ether and filtered to give pale yellow powder of 7β-[2-(2-tritylaminothiazol-4-yl)-(Z)-2-methoxyiminoacetamido]-3-[(1-acetamido-1H-tetrazol-5-yl)thiomethyl]-3-cephem-4-carboxylic acid (0.790 g, 92%), mp 167°–170° C. (decomposition).

IR $v_{max}^{Nujol}$ (cm$^{-1}$): 3220, 1770, 1715, 1680, 1520

NMR(DMSO-d$_6$)ppm: 2.17 (3H, s, —COCH$_3$), 3.64 (2H, broad s, H at 2nd position), 3.83 (3H, s, —COCH$_3$), 4.35 (2H, q, H at C$^{3'}$), 5.12 (2H, d, H at 6th position), 5.75 (2H, q, H at 7th position), 6,76 (1H, s, H at 5th position of thiazole), 7.34 (15H, s, benzene ring proton), 8,70 (1H, broad s, —NH-COCH$_3$), 9.50 (1H, d, —CONH—), 12.3 (1H, broad s, —COOH)

(d) 7β-[2-(2-Aminothiazol-4-yl)-(Z)-2-methoxyiminoacetamido]-3-[(1-acetamido-1H-tetrazol-5-yl)thiomethyl]-3-cephem-4-carboxylic acid A mixture of 7β-[2-(2-tritylaminothiazol-4-yl)-(Z)-2-methoxyiminoacetamido]-3-[(1-acetamido-1H-tetrazol-5-yl)thiomethyl]-3-cephem-4-carboxylic acid (0.560 g, 0.79 mmol) and 80% formic acid (3 ml) was stirred at room temperature for an hour. Then the mixture was treated in a manner similar to that described in Example 6, (d) to give pale yellow powder of sodium 7β-[2-(2-aminothiazol-4-yl)-(Z)-2-methoxyiminoacetamido]-3-[(1-acetamido-1H-tetrazol-5-yl)thiomethyl]-3-cephem-4-carboxylate (0.130 g, 28.5%), mp~200° C. (decomposition).

IR $\nu_{max}^{Nujol}$ (cm$^{-1}$): 3350, 1755, 1660, 1600, 1530

NMR(DMSO-d$_6$)ppm: 1.70 (3H, s, —COCH$_3$), 3.50 (2H, broad s, CH$_2$ at 2nd position), 3.84 (3H, s, —OCH$_3$), 4.20 (2H, broad s, CH$_2$ at C$^3$'), 5.04 (1H, d, H at 6th position), 5.60 (1H, q, H at 7th position), 6.70 (1H, s, H at 5th position of thiazole), 7.23 (2H, broad s, —NH$_2$), 8.25 (1H, broad s, —N$\underline{H}$—COCH$_3$), 9.50 (1H, d, —NHCO—)

EXAMPLE 9

7β-[2-(2-Aminothiazol-4-yl)-(Z)-2-n-butoxyiminoacetamido]-3-[(1-amino-1H-tetrazol-5-yl)thiomethyl]-3-cephem-4-carboxylic acid

(a) 1-Benzotriazolyl 2-(2-tritylaminothiazol-4-yl)-(Z)-2-n-butoxyiminoacetate To a solution of 2-(2-tritylaminothiazol-4-yl)-(Z)-2-n-butoxyiminoacetic acid (1.6 g, 3.29 mmol) and 1-hydroxybenzotriazole (0.49 g, 3.62 mmol) in tetrahydrofuran (16 ml) was added N,N'-dicyclohexylcarbodiimide (0.75 g, 3.62 mmol) and the mixture was stirred at room temperature. Then the mixture was treated in a manner similar to that descirbed in Example 6, (b) to give colorless needles of 1-benzotriazolyl 2-(2-tritylaminothiazol-4-yl)-(Z)-2-n-butoxyiminoacetate (1.50 g, 75.7%), mp 100°-102° C.

IR $\nu_{max}^{Nujol}$ (cm$^{-1}$): 3400, 1820, 1530, 1450, 1100, 970

(b) 7β-[2-(2-Tritylaminothiazol-4-yl)-(Z)-2-n-butoxyiminoacetamido]-3-[(1-amino-1H-tetrazol-5-yl)thiomethyl]-3-cephem-4-carboxylic acid A solution of 7β-amino-3-[(1-amino-1H-tetrazol-5-yl)thiomethyl]-3-cephem-4-carboxylic acid (0.653 g, 2 mmol), triethylamine (0.405 mg, 4 mmol) and 1-benzotriazolyl 2-(2-tritylaminothiazol-4-yl)-(Z)-2-n-butoxyiminoacetate (1.32 g, 2.2 mmol) in dimethylacetamide (6 ml) and water (0.6 mol) was treated in a manner similar to that described in Example 6, (c) to give pale brown powder of 7β-[2-(2-tritylaminothiazol-4-yl)-(Z)-2-n-butoxyiminoacetamido]-3-[(1-amino-1H-tetrazol-5-yl)thiomethyl]-3-cephem-4-carboxylic acid (0.535 g, 33.6%).

Rf: 0.37 (SiO$_2$, chloroform:ethyl acetate:methanol:acetic acid=5:5:1:1)

(c) 7β-[2-(2-Aminothiazol-4-yl)-(Z)-2-n-butoxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-n-butoxyiminoacetamido]-3-[(1-amino-1H-tetrazol-5-yl)thiomethyl]-3-cephem-4-carboxylic acid (0.500 g, 0.627 mmol) in 80% formic acid (2 ml) was treated in a manner similar to that described in Example 6, (d) to give pale brown powder of sodium 7β-[2-(2-aminothiazol-4-yl)-(Z)-2-n-butoxyiminoacetamido]-3-[(1-amino-1H-tetrazol-5-yl)thiomethyl]-3-cephem-4-carboxylate (100 mg, 27.5%).

IR $\nu_{max}^{Nujol}$ (cm$^{-1}$): 3300, 1755, 1660, 1600, 1525

NMR(DMSO-d$_6$)ppm: 0.94 (3H, t, J=6 Hz, CH$_3$), 1.2-1.8 (4H, m), 3.58 (2H, s, H at 2nd position), 4.1 (2H, t, J=6 Hz, —O—CH$_2$—CH$_2$—), 4.38 (2H, broad s, H at C$^3$'), 5.04 (1H, d, J=6 Hz, H at 6th position), 5.64 (1H, dd, J=6 and 8 Hz, H at 7th position), 6.74 (1H, s, H at 5th position of thiazole), 7.00 (2H, s, N—NH$_2$). 7.26 (2H, broad s, C—NH$_2$), 9.52 (1H, d, J=8 Hz, —CONH—)

EXAMPLE 10

7β-[2-(2-Aminothiazol-4-yl)-(Z)-2-(2-carbamoyl-2-propyloxyimino)acetamido]-3-[(1-amino-1H-tetrazol-5-yl)thiomethyl]-3-cephem-4-carboxylic acid

(a) 7β-[2-(2-tritylaminothiazol-4-yl)-(Z)-2-(2-carbamoyl-3-propyloxyimino)acetamido]-3-[(1-amino-1H-tetrazol-5-yl)thiomethyl]-3-cephem-4-carboxylic acid A solution of 2-(2-tritylaminothiazol-4-yl)-(Z)-2-(2-carbamoyl-2-propyloxyimino)acetic acid (2.00 g, 3.9 mmol), 1-hydroxybenzotriazole (0.560 g, 4.29 mmol) and N,N'-dicyclohexylcarbodiimide (0.840 g, 4.10 mmol) in dimethylacetamide (24 ml) was stirred at room temperature for 4 hours. To this solution was added a solution of 7β-amino-3-[(1-amino-1H-tetrazol-5-yl)thiomethyl]-3-cephem-4-carboxylic acid (1.41 g, 4.29 mmol) and triethylamine (0.790 g, 8.58 mmol) in dimethylacetamide (10 ml) and water (1.4 ml) and the mixture was allowed to react at room temperature for 17 hours. Then the mixture was treated in a manner similar to that described in Example 6, (c) to give pale yellow powder of 7β-[2-(2-tritylaminothiazol-4-yl)-(Z)-2-(2-carbamoyl-2-propyloxyimino)acetamido]-3-[(1-amino-1H-tetrazol-5-yl)thiomethyl]-3-cephem-4-carboxylic acid (2.27 g, 70.5%).

IR $\nu_{max}^{Nujol}$ (cm$^{-1}$): 3475, 3330, 3200, 1785, 1675, 1630 1600, 1540, 1170

NMR(DMSO-d$_6$)ppm: 1.35 (6H, s, CH$_3$×2), 3.65 (2H, m, CH$_2$ at 2nd position), 4.35 (2H, broad, CH$_2$ at C$^3$'), 5.10 (1H, d, J=5 Hz, H at 6th position), 5.60 (1H, m, H at 7th position), 6.70 (1H, s, H at 5th position of thiazole), 7.25 (15H, benzene ring proton), 8.80 (1H, broad, —CN$\underline{H}$—), 9.60 (1H, d, J=8 Hz, —CON$\underline{H}$—)

(b) 7β-[2-(2-Aminothiazol-4-yl)-(Z)-2-(2-carbamoyl-2-propyloxyimino)acetamido]-3-[(1-amino-1H-tetrazol-5-yl)thiomethyl]-3-cephem-4-carboxylic acid A solution of 7β-[2-(2-tritylaminothiazol-4-yl)-(Z)-2-(2-carbamoyl-2-propyloxyimino)acetamido]-3-[(1-amino-1H-tetrazol-5-yl)thiomethyl]-3-cephem-4-carboxylic acid (2.17 g, 2.64 mmol) in 80% formic acid (8 ml) was allowed to react at room temperature for an hour. Then the solution was treated in a manner similar to that described in Example 6, (d) to give pale yellow powder of sodium 7β-[2-(2-aminothiazol-4-yl)-(Z)-2-(2-carbamoyl-2-propyloxyimino)acetamido]-3-[(1-amino-1H-tetrazol-5-yl)thiomethyl]-3-cephem-4-carboxylate (0.56 g, 34.8%).

IR $\nu_{max}^{Nujol}$ (cm$^{-1}$): 3400 (shoulder), 3320, 3200, 1765, 1670, 1610, 1540, 1200, 1170, 960

NMR(DMSO-d$_6$)ppm: 1.35 (6H, s, CH$_3$×2), 4.35 (2H, broad, CH$_2$ at C$^3$'), 5.00 (1H, d, J=5 Hz, H at 6th position), 5.65 (1H, dd, J=8 and 5 Hz, H at 7th position), 6.70 (1H, s, H at 5th position of thiazole), 6.75-7.4 (6H, m), 9.60 (1H, d, J=8 Hz, —CONH—)

EXAMPLE 11

7β-[2-(2-Aminothiazol-4-yl)-(Z)-2-carbamoylmethoxyiminoacetamido]-3-[(1-amino-1H-tetrazol-5-yl)thiomethyl]-3-cephem-4-carboxylic acid (a)

7β-[2-(2-Tritylaminothiazol)-4-yl)-(Z)-2-carboxymethoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-carbamoylmethoxyiminoacetic acid (3.02 g, 6.2 mmol), 1-hydroxybenzotriazole (0.900 g, 6.7 mmol) and N,N'-dicyclohexylcarbodiimide (1.38 g, 6.7 mmol) in dimethylacetamide (17 ml) was stirred at 0°–5° C. for an hour. To the solution was added a solution of 7β-amino-3-[(1-amino-1H-tetrazol-5-yl)thiomethyl]-3-cephem-4-carboxylic acid (2.38 g, 7.2 mmol) and triethylamine (1.60 g, 15.8 mmol) in dimethylacetamide (12 ml) and water (2 ml) at the same temperature and allowed to react for 2 hours. Then the mixture was treated in a manner similar to that described in Example 6, (c) to give pale yellow powder of 7β-[2-(2-tritylaminothiazol-4-yl)-(Z)-2-carbamoylmethoxyiminoacetamido]-3-[(1-amino-1H-tetrazol-5-yl)thiomethyl]-3-cephem-4-carboxylic acid (3.43 g, 69.3%), mp~115° C. (decomposition).

IR $\nu_{max}^{Nujol}$ (cm$^{-1}$): 3200, 1775, 1675, 1600, 1530

(b)

7β-[2-(2-Aminothiazol-4-yl)-(Z)-2-carbamoylmethoxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-carbamoylmethoxyiminoacetamido]-3-[(1-amino-1H-tetrazol-5-yl)thiomethyl]-3-cephem-4-carboxylic acid (3.40 g, 4.26 mmol) in 80% formic acid (17 ml) was treated in a manner similar to that described in Example 6, (d) to give pale yellow powder of sodium 7β-[2-(2-aminothiazol-4-yl)-(Z)-2-carbamoylmethoxyiminoacetamido]-3-[(1-amino-1H-tetrazol-5-yl)thiomethyl]-3-cephem-4-carboxylate (750 mg, 47%), mp~220° C. (decomposition).

IR $\nu_{max}^{Nujol}$ (cm$^{-1}$): 3300, 1755, 1665, 1600, 1530, 1380

EXAMPLE 12

7β-[2-(2-Aminothiazol-4-yl)-(Z)-2-hydroxyiminoacetamido]-3-[(1-amino-1H-tetrazol-5-yl)thiomethyl]-3-cephem-4-carboxylic acid (a)

7β-[2-(2-tritylaminothiazol-4-yl)-(Z)-2-trityloxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-trityloxyiminoacetic acid (4.7 g, 7 mmol) (cf. Tetrahedron 1978, 34, 2233), 1-hydroxybenzotriazole (1.04 g, 7.7 mmol) and N,N'-dicyclohexylcarbodiimide (1.51 g, 7.35 mmol) in dimethylacetamide (27 ml) was allowed to react at room temperature for an hour. To the solution was added a solution of 7β-amino-3-[(1-amino-1H-tetrazol-4-yl)thiomethyl]-3-cephem-4-carboxylic acid (2.54 g, 7.7 mmol) and triethylamine (1.56 g, 15.4 mmol) in dimethylacetamide (20 ml) and water (0.5 ml) and the mixture was allowed to react at 5° C. for 1.5 hours. Then the mixture was treated in a manner similar to that described in Example 6, (c) to give pale yellow powder of 7β-[2-(2-tritylaminothiazol-4-yl)-(Z)-2-trityloxyiminoacetamido]-3-[(1-amino-1H-tetrazol-5-yl)thiomethyl]-3-cephem-4-carboxylic acid (2.86 g, 41.6%).

IR $\nu_{max}^{Nujol}$ (cm$^{-1}$): 1780, 1680, 1520, 1485

(b)

7β-[2-(2-Aminothiazol-4-yl)-(Z)-2-hydroxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-trityloxyiminoacetamido]-3-[(1-amino-1H-tetrazol-5-yl)thiomethyl]-3-cephem-4-carboxylic acid (1 g, 1 mmol) in 80% formic acid (5 ml) was treated in a manner similar to that described in Example 6 (d) to give pale brown powder of sodium 7β-[2-(2-aminothiazol-4-yl)-(Z)-2-hydroxyiminoacetamido]-3-[(1-amino-1H-tetrazol-5-yl)thiomethyl]-3-cephem-4-carboxylate (0.254 g, 25%).

IR $\nu_{max}^{Nujol}$ (cm$^{-1}$): 3320, 3200, 1760, 1610, 1530

NMR(DMSO-d$_6$)ppm: 4.32 (2H, broad s, CH$_2$ at C$^{3'}$), 4.95 (1H, d, J=4.8 Hz, H at 6th position), 5.6 (1H, m, H at 7th position), 6.57 (1H, s, H at 5th position of thiazole), 6.85 (2H, s, N—NH$_2$), 7.05 (1H, broad s, OH), 7.25 (2H, broad s, C—NH$_2$), 9.35 (1H, d, —CONH—)

EXAMPLE 13

7β-[2-(2-Aminothiazol-4-yl)-(Z)-2-methoxyiminoacetamido]-3-[(1-isopropylamino-1H-tetrazol-5-yl)thiomethyl]-3-cephem-4-carboxylic acid (a) 1-Isopropylidenamino-5-mercapto-1H-tetrazole sodium salt A solution of 1-amino-5-mercapto-1H-tetrazole (4.86 g) in acetone (50 ml) was stirred for 1.5 hours, and the reaction solution was evaporated to remove solvent. Acetone was added to the residue, and the acetone solution was evaporated again to remove solvent. The residue was treated with acetone twice in the same manner as above, the resulting residue was dissolved in 40 ml of acetone, and 2-ethylhexanoic acid sodium salt (10.0 g) was added thereto. The mixture was stirred at room temperature for 30 minutes. Ether (40 ml) was added to the mixture, and crystalline precipitates were collected by filtration. 5.65 g of 1-isopropylidenamido-5-mercapto-1H-tetrazole sodium salt were obtained as colorless needles. mp 162.5°–164° C. (decomp.)

IR $\nu_{max}^{Nujol}$ (cm$^{-1}$): 3530, 3175, 1640, 1620, 1350, 1260, 1170, 1120

(b) 1-Isopropylamino-5-mercapto-1H-tetrazole

1-Isopropylidenamino-5-mercapto-1H-tetrazole sodium salt (5.37 g) was dissolved in a mixture of tetrahydrofuran (24 ml) and methanol (24 ml), and sodium borohydride (1.14 g) was added gradually thereto at 5°–6° C. under stirring. The mixture was stirred at the same temperature for one hour, and then at room temperature for one hour. The mixture was evaporated to remove solvent, and the residue was dissolved in icewater. The aqueous solution was adjusted to pH 2.8 with 6N-hydrochloric acid, and the solution was extracted with ethyl acetate (20 ml) three times repeatedly. The extracts were washed with a saturated sodium chloride solution, dried and then evaporated to remove solvent. n-Hexane was added to the residue thus obtained, and crystalline precipitates were collected by filtration. 4.14 g of 1-isopropylamino-5-mercapto-1H-tetrazole were obtained as colorless needles. mp 92°–95° C.

IR $\nu_{max}^{Nujol}$ (cm$^{-1}$): 3262, 3076, 3018, 2803, 2777, 1522

NMR (CDCl$_3$) δ: 1.2 (d, J=6 Hz, CH$_3$×2), 3.75 (d,d, 1H, J=6 Hz, —CH(CH$_3$)$_2$), 5.0–6.2 (broad, 1H, NH)

(c)

7β-(Amino-3-[(1-isopropylamino-1H-tetrazol-5-yl)thiomethyl]-3-cephem-4-carboxylic acid:

To a solution of sodium hydrogen bicarbonate (1 g, 12 mmol) in water (80 ml) were added 7β-aminocephalosporanic acid (3 g, 11 mmol) and 1-isopropylamino-5-mercapto-1H-tetrazole sodium salt (4 g, 22 mmol). The mixture was treated in a manner similar to that described in Example 6, (a) to give pale brown powder of 7β-amino-3-[(1-isopropylamino-1H-tetrazol-5-yl)thiomethyl]-3-cephem-4-carboxylic acid (2.7 g, 66%).

IR $\nu_{max}^{Nujol}$ (cm$^{-1}$): 1802, 1620, 1543, 1414, 1350

NMR(DMSO-d$_6$-CF$_3$COOH)ppm: 1.05 (6H, d, J=6 Hz, CH$_3$×2), 3.2–3.9 (3H, m, —C$\underline{\text{H}}$(CH$_3$)$_2$ and CH$_2$ at 2nd position), 4.4 (2H, dd, J=8.4 and 13.2 Hz, CH$_2$ at C$^{3'}$), 5.1 (2H, s, H at 6th and 7th positions)

(d)

7β-[2-(2-Tritylaminothiazol-4-yl)-(Z)-2-methoxyiminoacetamido]-3-[(1-isopropylamino-1H-tetrazol-5-yl)thiomethyl]-3-cephem-4-carboxylic acid To a solution of 7β-amino-3-[(1-isopropylamino-1H-tetrazol-5-yl)thiomethyl]-3-cephem-4-carboxylic acid (1.35 g, 3.63 mmol) and triethylamine (0.735 mg, 7.26 mmol) in dimethylacetamide (17 ml) was added 1-benzotriazolyl 2-(2-tritylaminothiazol-4-yl)-(Z)-2-methoxyiminoacetate (3.05 g, 5.44 mmol). The mixture was treated in a manner similar to that described in Example 6, (c) to give pale brown powder of 7β-[2-(2-tritylaminothiazol-4-yl)-(Z)-2-methoxyiminoacetamido]-3-[(1-isopropylamino-1H-tetrazol-5-yl)thiomethyl]-3-cephem-4-carboxylic acid (2.45 g, 84.8%).

IR $\nu_{max}^{Nujol}$ (cm$^{-1}$): 1780, 1680, 1620, 1590, 1535, 1490

(e)

7β-[2-(2-Aminothiazol-4-yl)-(Z)-2-methoxyiminoacetamido]-3-[(1-isopropylamino-1H-tetrazol-5-yl)thiomethyl]-3-cephem-4-carboxylic acid A solution of 7β-[2-(2-tritylaminothiazol-4-yl)-(Z)-2-methoxyiminoacetamido]-3-[(1-isopropylamino-1H-tetrazol-5-yl)thiomethyl]-3-cephem-4-carboxylic acid (2.45 g, 3.07 mmol) in 80% formic acid (12 ml) was treated in a manner similar to that described in Example 6, (d) to give sodium 7β-[2-(2-aminothiazol-4-yl)-(Z)-2-methoxyiminoacetamido]-3-[(1-isopropylamino-1H-tetrazol-5-yl)thiomethyl]-3-cephem-4-carboxylate (0.638 g, 36%).

IR $\nu_{max}^{Nujol}$ (cm$^{-1}$): 1766, 1667, 1606, 1535

NMR(DMSO-d$_6$)ppm: 1.00 (6H, d, J=6.3 Hz, CH$_3$×2), 3.83 (3H, s, OCH$_3$), 4.35 (2H, broad s, CH$_2$ at C$^{3'}$), 4.97 (1H, d, J=4.7 Hz, H at 6th position), 5.6 (1H, m, H at 7th position), 6.67 (1H, s, H at thiazole), 7.18 (2H, broad s, C—NH$_2$), 7.25 (1H, d, J=3.2 Hz, N—NH), 9.52 (1H, d, J=7.7 Hz, —CONH—)

EXAMPLE 14

7β-[2-(2-Aminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid (a)

7β-[2-(2-Tritylaminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-(N-methylcarbamoyl)methoxyiminoacetic acid (3.25 g, 6.5 mmol), 1-hydroxybenzotriazole (0.97 g, 7.15 mmol) and N,N'-dicyclohexylcarbodiimide (1.41 g, 6.83 mmol) in dimethylacetamide (34 ml) was stirred at room temperature for 4 hours. To the solution was added a solution of 7β-amino-3-[(1-amino-1H-tetrazol-5-yl)thiomethyl]-3-cephem-4-carboxylic acid (2.57 g, 7.8 mmol) and triethylamine (1.73 g, 17.2 mmol) in dimethylacetamide (20 ml) and water (2.4 ml) and the mixture was stirred at room temperature for 17 hours. Then the mixture was treated in a manner similar to that described in Example 6, (c) to give pale brown powder of 7β-[2-(2-tritylaminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid (4.1 g, 78%).

IR $\nu_{max}^{Nujol}$ (cm$^{-1}$): 3320, 3230, 1875, 1660, 1540, 1065

NMR(DMSO-d$_6$)ppm: 2.60 (3H, d, J=5 Hz, NHC$\underline{\text{H}}_3$), 3.65 (2H, broad, H at 2nd position), 4.25 (2H, m, H at C$^{3'}$), 4.45 (2H, broad s, —OCH$_2$), 5.10 (1H, d, J=5 Hz, H at 6th position)

(b)

7β-[2-(2-Aminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid (2.1 g, 2.59 mmol) in 80% formic acid (8 ml) was treated in a manner similar to that described in Example 6, (d) to yield pale brown powder of 7β-[2-(2-aminothiazol-4-yl)-(Z)-2-(N-methylcarbamoyl)methoxyiminoacetamido]-3-[(1-amino-1H-tetrazol-5-yl)thiomethyl]-3-cephem-4-carboxylic acid (1.25 g, 85%).

IR $\Gamma_{max}^{Nujol}$ Icm$^{-1}$): 3320, 3200, 1775, 1660, 1540, 1260, 1060

NMR(DMSO-d$_6$)ppm: 2.65 (3H, d, J=5 Hz, NHC$\underline{\text{H}}_3$), 3.65 (2H, broad, H at 2nd position), 4.25 (2H, m, H at C$^{3'}$), 4.45 (2H, broad s, —OCH$_2$—), 5.10 (1H, d, J=5 Hz, H at 6th position), 5.80 (1H, m, H at 7th position), 6.70 (1H, s, H at 5th position of thiazole), 6.7–7.5 (6H, m), 9.65 (1H, d, J=8 Hz, —CONH—)

EXAMPLE 15

7β-[2-(2-Aminothiazol-4-yl)-(Z)-2-(carboxymethoxyimino)acetamido]-3-[(1-amino-1H-tetrazol-5-yl)thiomethyl]-3-cephem-4-carboxylic acid (a)

7β-[2-(2-Tritylaminothiazol-4-yl)-(Z)-2-(tert-butoxycarbonylmethoxyimino)acetamido]-3-[(1-amino-1H-tetrazol-5-yl)thiomethyl]-3-cephem-4-carboxylic acid A solution of 2-(2-tritylaminothiazol-4-yl)-(Z)-2-(tert-butoxycarbonylmethoxyimino)acetic acid (3.80 g, 7 mmol), 1-hydroxybenzotriazole (1.09 g, 8.05 mmol) and N,N'-dicyclohexylcarbodiimide (1.59 g, 7.7 mmol) in dimethylacetamide (40 ml) was stirred at room temperature for 2 hours. To the solution was added a solution of 7β-amino-3-[(1-amino-1H-tetrazol-5-yl)thiomethyl]-3-cephem-4-carboxylic acid (2.76 g, 8.4 mmol) and triethylamine (1.70 g, 16.8 mmol) in dimethylacetamide (20 ml) and water (2.8 ml) and the mixture was stirred at room temperature for 17 hours. Then the mixture was treated in a manner similar to that described in Example 6, (c) to give pale brown powder of 7β-[2-(2-tritylaminothiazol-4-yl)-(Z)-2-(tert-butoxycarbonylmethoxyimino)acetamido]-3-[(1-amino-1H-tetrazol-5-yl)thiomethyl]-3-cephem-4-carboxylic acid (4.96 g, 83%).

IR $\nu_{max}^{Nujol}$ (cm$^{-1}$): 3250, 2800–2300, 1780, 1730, 1680, 1530, 1250, 1160, 1100, 1070

NMR(DMSO-d$_6$)ppm: 1.40 (9H, s, CH$_3$×3), 3.60 (2H, broad, CH$_2$ at 2nd position), 4.30 (2H, m, CH$_2$ at C$^{3'}$), 4.50 (2H, broad s, —OCH$_2$), 5.10 (1H, J=5 Hz, H at 6th position), 5.65 (1H, m, H at 7th position), 6.70 (1H, s, H at 5th position of thiazole), 7.0 (2H, broad s, NH$_2$), 7.25 (15H, s, benzene ring proton, 9.35 (1H, d, J=8 Hz, —CONH—)

(b)
7β-[2-(2-Aminothiazol-4-yl)-(Z)-2-(carboxymethoxyimino)acetamido]-3-[(1-amino-1H-tetrazol-5-yl)thiomethyl]-3-cephem-4-carboxylic acid A solution of 7β-[2-(2-tritylaminothiazol-4-yl)-(Z)-2-(tert-butoxycarbonylmethoxyimino)acetamido]-3-[(1-amino-1H-tetrazol-5-yl)thiomethyl]-3-cephem-4-carboxylic acid (4.80 g, 5.6 mmol) in trifluoroacetic acid (48 ml) was stirred at room temperature for 40 minutes. Trifluoroacetic acid was removed by evaporation and the residue was washed with ether. To the residue was added 80% formic acid (10 ml) and the mixture was stirred at room temperature for 40 minutes. Then the mixture was treated in a manner similar to that described in Example 6, (d) to give pale brown powder of crude 7β-[2-(2-aminothiazol-4-yl)-(Z)-2-(carboxymethoxyimino)acetamido]-3-[(1-amino-1H-tetrazol-5-yl)thiomethyl]-3-cephem-4-carboxylic acid (1.17 g).

The crude acid (1.17 g) was treated with sodium 2-ethylhexanoate (1.1 g) to give disodium salt, which was chromatographed on Amberlite XAD-4 column and eluted with water. The eluate was lyophilized to give pale yellow powder of purified disodium salt (0.225 g, 6.7%).

IR $\nu_{max}^{Nujol}$ (cm$^{-1}$): 3300, 1765, 1660 (shoulder), 1600, 1540, 1040

NMR(DMSO-d$_6$)ppm: 4.35 (4H, broad, —OCH$_2$— and CH$_2$ at C$^{3'}$), 5.00 (1H, d, J=5 Hz, H at 6th position), 5.65 (1H, m, H at 7th position), 6.80 (1H, s, H at 5th position of thiazole), 6.90 (2H, broad, N—NH$_2$), 7.20 (2H, broad, —CNH$_2$), 11.45 (1H, d, J=8 Hz, —CONH—)

EXAMPLE 16

7β-[2-(2-Aminothiazol-4-yl)-(Z)-2-(1-carboxyethoxyimino)acetamido]-3-[(1-amino-1H-tetrazol-5-yl)thiomethyl]-3-cephem-4-carboxylic acid (a)
7β-[2-(2-Tritylaminothiazol-4-yl)-(Z)-2-(1-tert-butoxycarbonylethoxyimino)acetamido]-3-[(1-amino-1H-tetrazol-5-yl)thiomethyl]-3-cephem-4-carboxylic acid A solution of 2-(2-tritylaminothiazol-4-yl)-(Z)-2-(1-tert-butoxycarbonylethoxyimino)acetic acid (4.18 g, 7.5 mmol), 1-hydroxybenzotriazole (1.11 g, 8.25 mmol) and N,N'-dicyclohexylcarbodiimide (1.70 g, 8.25 mmol) in dimethylacetamide (35 ml) was stirred at room temperature for 2.5 hours. To the solution was added a solution of 7β-amino-3-[(1-amino-1H-tetrazol-5-yl)thiomethyl]-3-cephem-4-carboxylic acid (2.96 g, 8.98 mmol) and triethylamine (1.82 g, 18 mmol) in dimethylacetamide (18 ml) and water (2.5 ml) and the mixture was stirred at room temperature for 17 hours. Then the mixture was treated in a manner similar to that described in Example 6, (c) to give pale brown powder of 7β-[2-(2-tritylaminothiazol-4-yl)-(Z)-2-(1-tert-butoxycarbonylethoxyimino)acetamido]-3-[(1-amino-1H-tetrazol-5-yl)thiomethyl]-3-cephem-4-carboxylic acid (3.88 g, 60%).

IR $\nu_{max}^{Nujol}$ (cm$^{-1}$): 3250, 2800–2300, 1780, 1730, 1680, 1530, 1250, 1160, 1100

NMR(DMSO-d$_6$)ppm: 1.40 (12H, 3×CH$_3$), 3.65 (2H, broad, CH$_2$ at 2nd position), 3.9–4.9 (3H, CH$_2$ at C$^{3'}$ and —O—CH—), 5.10 (1H, d, J=5 Hz, H at 6th position), 5.70 (1H, m, H at 7th position), 6.75 (1H, s, H at 5th position of thiazole), 7.30 (15H, H on benzene ring), 9.30 (1H, d, J=8 Hz, —CONH—)

(b)
7β-[2-(2-Aminothiazol-4-yl)-(Z)-2-(1-carboxyethoxyimino)acetamido]-3-[(1-amino-1H-tetrazol-5-yl)thiomethyl]-3-cephem-4-carboxylic acid A solution of 7β-[2-(2-tritylaminothiazol-4-yl)-(Z)-2-(1-tert-butoxycarbonylethoxyimino)acetamido]-3-[(1-amino-1H-tetrazol-5-yl)thiomethyl]-3-cephem-4-carboxylic acid (1.48 g, 1.7 mmol) in 80% formic acid (6 ml) was stirred at room temperature for an hour. To the solution was added water (30 ml) and the precipitates formed were removed by filtration. The filtrate was concentrated and the residue was treated with ether to give 2-aminothiazole derivative (1.10 g). The 2-aminothiazole compound was dissolved in trifluoroacetic acid (8 ml) and the solution was stirred at room temperature for an hour. The trifluoroacetic acid was removed by evaporation. The residue was triturated with ether to solidify it, and ethanol was added thereto (10 ml). The mixture was stirred at 50° C. for 30 minutes. After cooling, the precipitates were filtered to give pale brown powder of crude 7β-[2-(2-aminothiazol-4-yl)-(Z)-2-(1-carboxyethoxyimino)acetamido]-3-[(1-amino-1H-tetrazol-5-yl)thiomethyl]-3-cephem-4-carboxylic acid (0.41 g). The crude acid was dissolved in aqueous sodium hydrogen carbonate. The solution was chromatographed on Amberlite XAD-4 column and eluted with water:ethanol (100:7). The eluate was lyophilized to give disodium salt (0.145 g, 14%).

IR $\nu_{max}^{Nujol}$ (cm$^{-1}$): 3300, 1760, 1660 (shoulder), 1540, 1100, 1040

NMR(DMSO-d$_6$)ppm: 1.40 (3H, broad, CH$_3$), 4.0–4.7 (3H, CH$_2$ at C$^{3'}$ and —OCH—), 5.0 (1H, d, J=5 Hz, H at 6th position), 5.65 (1H, m, H at 7th position), 6.8 (1H, s, H at 5th position of thiazole), 6.9 (2H, broad, —NNH$_2$), 7.20 (2H, broad, $C-NH_2$)

EXAMPLE 17

7β-[2-(2-Aminothiazol-4-yl)-(Z)-2-n-propoxyiminoacetamido]-3-[(1-amino-1H-tetrazol-5-yl)thiomethyl]-cephem-4-carboxylic acid (a)

7β-[2-(2-Tritylaminothiazol-4-yl)-(Z)-2-n-propoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-n-propoxyiminoacetic acid (3.77 g, 8 mmol), 1-hydroxybenzotriazole (1.19 g, 8.8 mmol) and N,N'-dicyclohexylcarbodiimide (1.81 g, 8.8 mmol) in tetrahydrofuran (50 ml) was stirred at 0°–5° C. for 4 hours. The solution was treated in a manner similar to that described in Example 6, (b) to give activated ester (4.92 g), mp ~105° C. (decomposition).

IR $\nu_{max}^{Nujol}$ (cm$^{-1}$): 3310, 2925, 1829, 1532

The activated ester (2.94 g, 5 mmol) was added to a solution of 7β-amino-3-[(1-amino-1H-tetrazol-5-yl)thiomethyl]-3-cephem-4-carboxylic acid (1.65 g, 5 mmol) and triethylamine (1.20 g, 12 mmol) in dimethylacetamide (20 ml) and water (0.3 ml) and the mixture was stirred at 0°–5° C. for 4 hours. Then the mixture was treated in a manner similar to that described in Example 6, (c) to give pale yellow powder of 7β-[2-(2-tritylaminothiazol-4-yl)-(Z)-2-n-propoxyiminoacetamido]-3-[(1-amino-1H-tetrazol-5-yl)thiomethyl]-3-cephem-4-carboxylic acid (1.75 g, 48%), mp ~115° C.

IR $\nu_{max}^{Nujol}$ (cm$^{-1}$): 3240, 1775, 1675, 1515

Rf: 0.4 (SiO$_2$, chloroform:ethyl acetate:methanol:acetic acid = 5:5:1:1)

(b)

7β-[2-(2-Aminothiazol-4-yl)-(Z)-2-n-propoxyiminoacetamido]-3-[1-amino-1H-tetrazol-5-yl)thiomethyl]-3-cephem-4-carboxylic acid A solution of 7β-[2-(2-tritylaminothiazol-4-yl)-(Z)-2-n-propoxyiminoacetamido]-3-[(1-amino-1H-tetrazol-5-yl)thiomethyl]-3-cephem-4-carboxylic acid (1.7 g, 2.17 mmol) in 80% formic acid (5.5 ml) was treated in a manner similar to that described in Example 6, (d) to give pale yellow powder of sodium 7β-[2-(2-aminothiazol-4-yl)-(Z)-2-n-propoxyiminoacetamido]-3-cephem-4-carboxylate (0.50 g, 41%).

IR $\nu_{max}^{Nujol}$ (cm$^{-1}$): 3330, 1770, 1675, 1600, 1540

Rf: 0.37 (SiO$_2$, n-butanol:acetic acid:water = 4:1:3)

EXAMPLE 18

7β-[2-(2-Aminothiazol-4-yl)-(Z)-2-(2-hydroxyethoxyimino)acetamido]-3-[(1-amino-1H-tetrazol-5-yl)thiomethyl]-3-cephem-4-carboxylic acid (a)

7β-[2-(2-Tritylaminothiazol-4-yl)-(Z)-2-[2-(tetrahydro-2H-pyran-2-yl)oxy]ethoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-[2-(tetrahydro-2H-pyran-2-yl)oxy]ethoxyiminoacetic acid (2.5 g, 4.4 mmol), 1-hydroxybenzotriazole (0.65 g, 4.8 mmol) and N,N'-dicyclohexylcarbodiimide (0.99 g, 4.8 mmol) in tetrahydrofuran (25 ml) was stirred at 0°–5° C. for 2.5 hours. The solution was treated in a manner similar to that described in Example 6, (b) to give pale yellow needles of activated ester (2.60 g, 88%), mp 164°–165° C. (decomposition).

IR $\nu_{max}^{Nujol}$ (cm$^{-1}$): 3390, 1826, 1527, 1506

Rf: 0.58 (SiO$_2$, n-hexane:ethyl acetate = 1:1)

The activated ester (3.37 g, 5 mmol) was added to a solution of 7β-amino-3-[(1-amino-1H-tetrazol-5-yl)thiomethyl]-3-cephem-4-carboxylic acid (1.65 g, 5 mmol) and triethylamine (1.20 g, 12 mmol) in dimethylacetamide (20 ml) and water (0.3 ml) and the mixture was stirred at room temperature for 4 hours. Then the mixture was treated in a manner similar to that described in Example 6, (c) to give pale yellow powder of 7β-[2-(2-tritylaminothiazol-4-yl)-(Z)-2-[2-(tetrahydro-2H-pyran-2-yl)oxy]ethoxyiminoacetamido]-3-[(1-amino-1H-tetrazol-5-yl)thiomethyl]-3-cephem-4-carboxylic acid (2.25 g, 51.8%).

IR $\nu_{max}^{Nujol}$ (cm$^{-1}$): 3230, 1786, 1683, 1596

Rf: 0.38 (SiO$_2$, chloroform:ethyl acetate:methanol:acetic acid = 5:5:1:1)

(b)

7β-[2-(2-Aminothiazol-4-yl)-(Z)-2-(2-hydroxyethoxyimino)acetamido]-3-[(1-amino-1H-tetrazol-5-yl)thiomethyl]-3-cephem-4-carboxylic acid A solution of 7β-[2-(2-tritylaminothiazol-4-yl)-(Z)-2-[2-(tetrahydro-2H-pyran-2-yl)-oxy]ethoxyiminoacetamido]-3-[(1-amino-1H-tetrazol-5-yl)thiomethyl]-3-cephem-4-carboxylic acid (1.25 g, 1.4 mmol) in 80% formic acid (5 ml) was treated in a manner similar to that described in Example 6, (d) to give crude sodium 7β-[2-(2-aminothiazol-4-yl)-(Z)-2-(2-hydroxyethoxyimino)acetamido]-3-cephem-4-carboxylate. The crude sodium salt was chromatographed on Amberlite XAD-4 column and eluted with water:ethanol (9:1). The eluate was lyophilized to give purified sodium salt of pale yellow powder (0.06 g, 7.6%).

Rf: 0.31 (SiO$_2$, n-butanol:acetic acid:water = 4:1:2)

NMR(DMSO-d$_6$)ppm: 3.6 (4H, m), 4.1 (2H, m), 4.35 (2H, m, CH$_2$ at C$^3$'), 5.0 (1H, d, J=4 Hz, H at 6th position), 5.65 (1H, dd, J=4 and 8 Hz), 6.75 (1H, s, H at 5th position of thiazole), 6.95 (2H, s, N—NH$_2$), 7.25 (2H, s, C—NH$_2$), 9.45 (1H, d, J=8 Hz, —CONH—)

EXAMPLE 19

7β-[2-(2-Aminothiazol-4-yl)-(Z)-2-methoxyiminoacetamido]-3-[(1-ethylamino-1H-tetrazol-5-yl)thiomethyl]-3-cephem-4-carboxylic acid (a) 1-Ethylamino-5-mercapto-1H-tetrazole 1-Acetoamido-5-mercapto-1H-tetrazole (1.59 g) was dissolved in anhydrous tetrahydrofuran (27 ml), and the mixture was refluxed. 70% Sodium bis(2-methoxyethoxy)aluminum hydride-toluene solution (5 ml) was added dropwise thereto under stirring. After the addition, the mixture was refluxed for 4 hours. The reaction mixture was evaporated under reduced pressure to remove solvent. Ice-water was added to the residue, and the aqueous solution thus obtained was adjusted to pH 3 with 20% sulfuric acid. The mixture was salted out with sodium chloride, and extracted with ethyl acetate. The extracts were washed with a saturated sodium chloride solution, dried and then evaporated to remove solvent. The residue was recrystallized from isopropyl ether-hexane (1:2) to give 0.97 g of 1-ethylamino-5-mercapto-1H-tetrazole as colorless prisms. mp 90°–91° C.

IR $\nu_{max}^{Nujol}$ (cm$^{-1}$): 3200, 3080, 1520

Mass m/e: 145 (M$^+$), 117 (M$^+$—N$_2$), 103 (base peak)

(b)
7β-[2-(2-aminothiazol-4-yl)-(Z)-2-methoxyiminoacetamido]-3-[(1-ethylamino-1H-tetrazol-5-yl)thiomethyl]-3-cephem-4-carboxylic acid A solution of sodium 7β-[2-(2-aminothiazol-4-yl)-(Z)-2-methoxyiminoacetamido]-3-acetoxy-3-cephem-4-carboxylate (0.955 g, 2 mmol) and 1-ethylamino-5-mercapto-1H-tetrazole sodium salt (0.500 g, 3 mmol) in phosphate buffer (pH 6.4, 30 ml) was stirred at 60° C. for 7.5 hours. Then the solution was treated in a manner similar to that described in Example 7, treated with Amberlite XAD-4 column and eluted. The eluate was lyophilized to give pale yellow powder of sodium 7β-[2-(2-aminothiazol-4-yl)-(Z)-2-methoxyiminoacetamido]-3-[(1-ethylamino-1H-tetrazol-5-yl)thiomethyl]-3-cephem-4-carboxylate (0.450 g, 40%).

IR$\nu_{max}^{Nujol}$ (cm$^{-1}$): 3315, 1766, 1665, 1604, 1536, 1043

Rf: 0.51 (SiO$_2$, n-butanol:acetic acid:water=4:1:2)

NMR(DMSO-d$_6$)ppm: 1.00 (3H, t, J=6 Hz, CH$_2$CH$_3$), 3.89 (3H, s, OCH$_3$), 4.35 (2H, broad, CH$_2$ at C$^3$'), 5.00 (1H, d, J=4.8 Hz, H at 6th position), 5.65 (1H, m, H at 7th position), 6.70 (1H, s, H at 5th position of thiazole), 7.00-7.50 (3H, m, —C—NH$_2$ and —N—NH—), 9.45 (1H, d, J=8 Hz, —CONH—)

EXAMPLE 20

7β-[2-(2-Aminothiazol-4-yl)-(Z)-2-methoxyiminoacetamido]-3-[(1-methylamino-1H-tetrazol-5-yl)thiomethyl]-3-cephem-4-carboxylic acid (a) 1-Methylamino-5-mercapto-1H-tetrazole 1-Formamido-5-mercapto-1H-tetrazole (4.35 g) was dissolved in anhydrous tetrahydrofuran (120 ml), and the mixture was refluxed. 70% Sodium bis(2-methoxyethoxy)aluminum hydride-toluene solution (20 ml) was added dropwise thereto under stirring. After the addition, the mixture was refluxed for one hour. The reaction mixture was evaporated under reduced pressure to remove solvent. The residue thus obtained was treated in the same manner as described in Example 19(a). The residue thus obtained was recrystallized from a mixture of isopropanol-n-hexane (1:3) to give 3.15 g of 1-methylamino-5-mercapto-1H-tetrazole as colorless prisms. mp 138°-139° C. (decomp.)

IR$\nu_{max}^{Nujol}$ (cm$^{-1}$): 3200, 3080, 1525, 1300, 1200, 1160, 1050, 980

(b)
7β-[2-(2-Aminothiazol-4-yl)-(Z)-2-methoxyiminoacetamido]-3-[(1-methylamino-1H-tetrazol-5-yl)thiomethyl]-3-cephem-4-carboxylic acid A solution of sodium 7β-[2-(2-aminothiazol-4-yl)-(Z)-2-methoxyiminoacetamido]-3-acetoxy-3-cephem-4-carboxylate (1.43 g, 3 mmol), 1-methylamino-5-mercapto-1H-tetrazole (0.590, 4.5 mmol) and sodium hydrogen carbonate (0.378 g, 4.5 mmol) in phosphate buffer (pH 6.4, 45 ml) was stirred at 60° C. for 8 hours. Then the solution was treated in a manner similar to that described in Example 7 to give pale yellow powder of sodium 7β-[2-(2-aminothiazol-4-yl)-(Z)-2-methoxyiminoacetamido]-3-[(1-methylamino-1H-tetrazol-5-yl)thiomethyl]-3-cephem-4-carboxylate (0.73 g, 44%).

IR$\nu_{max}^{Nujol}$ (cm$^{-1}$): 3304, 1766, 1662, 1602, 1536, 1040

Rf: 0.48 (SiO$_2$, n-butanol:acetic acid:water=4:1:2)

NMR(DMSO-d$_6$)ppm: 3.83 (3H, s, OCH$_3$), 4.34 (2H, broad, CH$_2$ at C$^3$'), 5.00 (1H, d, J=4.9 Hz, H at 6th position), 5.60 (1H, dd, J=4.6 and 8.2 Hz, H at 7th position), 6.70 (1H, s, H at 5th position of thiazole), 7.20 (3H, broad, C—NH$_2$ and N—NH), 9.45 (1H, d, J=8.2 Hz, —CONH—)

EXAMPLE 21

7β-[2-(2-Aminothiazol-4-yl)-(Z)-2-ethoxyiminoacetamido]-3-[(1-amino-1H-tetrazol-5-yl)thiomethyl]-3-cephem-4-carboxylic acid (a)
7β-[2-(2-Tritylaminothiazol-4-yl)-(Z)-2-ethoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-ethoxyiminoacetic acid (5.00 g, 10.9 mmol), 1-hydroxybenzotriazole (1.62 g, 12.0 mml) and N,N'-dicyclohexylcarbodiimide (2.50 g, 12.0 mmol) in tetrahydrofuran (50 ml) was stirred at 5° C. for 4 hours. The solution was treated in a manner similar to that described in Example 6, (b) to give pale yellow needles of activated ester (5.55 g, 88.6%), mp 170°-173° C. (decomposition).

IR$\nu_{max}^{Nujol}$ (cm$^{-1}$): 3400, 1824, 1533, 1510

Rf: 0.46 (SiO$_2$, n-hexane-ethyl acetate=1:1)

The activated ester (5.50 g, 9.56 mmol) was added to a solution of 7β-amino-3-[(1-amino-1H-tetraozol-5-yl)thiomethyl]-3-cephem-4-carboxylic acid (2.20 g, 6.70 mmol) and triethylamine (1.46 g, 14.5 mmol) in dimethylacetamide (26 ml) and water (0.3 ml) and the mixture was stirred at 0°-5° C. for 5 hours. Then the mixture was treated in a manner similar to that described in Example 6, (c) to give pale yellow powder of 7β-[2-(2-tritylaminothiazol-4-yl)-(Z)-2-ethoxyiminoacetamido]-3-[(1-amino-1H-tetrazol-5-yl)thiomethyl]-3-cephem-4-carboxylic acid (3.00 g, 58.2%), mp ∼145° C. (decomposition).

IR$\nu_{max}^{Nujol}$ (cm$^{-1}$): 3217, 1784, 1683, 1596

Rf: 0.30 (SiO$_2$, chloroform:ethyl acetate:methanol:acetic acid=5:5:1:1)

(b)
7β-[2-(2-Aminothiazol-4-yl)-(Z)-2-ethoxyiminoacetamido]-3-[1-amino-1H-tetrazol-5-yl)thiomethyl]-3-cephem-4-carboxylic acid A solution of 7β-[2-(2-tritylaminothiazol-4-yl)-(Z)-2-ethoxyiminoacetamido]-3-[(1-amino-1H-tetrazol-5-yl)thiomethyl]-3-cephem-4-carboxylic acid (2.80 g, 3.64 mmol) in 80% formic acid (15 ml) was treated in a manner similar to that described in Example 6, (d) to give pale yellow powder of sodium 7β-[2-(2-aminothiazol-4-yl)-(Z)-2-ethoxyiminoacetamido]-3-[(1-amino-1H-tetrazol-5-yl)thiomethyl]-3-cephem-4-carboxylate (1.01 g, 52.8%), mp ∼220° C. (decomposition).

IR$\nu_{max}^{Nujol}$ (cm$^{-1}$): 3326 (broad), 1765, 1670, 1601, 1535

Rf: 0.37 (SiO$_2$, n-butanol:acetic acid:water=4:1:2)

EXAMPLE 22

7β-[2-(2-Aminothiazol-4-yl)-(Z)-2-isopropoxyiminoacetamido]-3-[(1-amino-1H-tetrazol-5-yl)thiomethyl]-3-cephem-4-carboxylic acid (a)

7β-[2-(2-Tritylaminothiazol-4-yl)-(Z)-2-isopropoxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-isopropoxyiminoacetic acid (3.06 g, 6.5 mmol), 1-hydroxybenzotriazole (1.01 g, 7.47 mmol) and N,N'-dicyclohexylcarbodiimide (1.47 g, 7.15 mmol) in dimethylacetamide (36 ml) was stirred at room temperature for 3 hours. To the solution was added a solution of 7β-amino-3-[(1-amino-1H-tetrazol-5-yl)thiomethyl]-3-cephem-4-carboxylic acid (2.35 g, 7.15 mmol) and triethylamine (1.44 g, 14.2 mmol) in dimethylacetamide (18 ml) and water (2.4 ml) and the mixture was stirred at room temperature for 17 hours. Then the mixture was treated in a manner similar to that described in Example 6, (c) to give pale brown powder of 7β-[2-(2-tritylaminothiazol-4-yl)-(Z)-2-isopropoxyiminoacetamido]-3-[(1-amino-1H-tetrazol-5-yl)thiomethyl]-3-cephem-4-carboxylic acid (3.10 g, 61%).

IR$\nu_{max}^{Nujol}$ (cm$^{-1}$): 3210, 1785, 1680, 1045, 1000

NMR(DMSO-d$_6$)ppm: 1.20 (6H, d, J=5 Hz, CH(CH$_3$)$_2$, 5.10 (1H, d, J=5 Hz, H at 6th position), 5.70 (1H, dd, J=5 and 8 Hz, H at 7th position), 6.65 (1H, s, H at 5th position of thiazole), 7.30 (15H, s, H on benzene ring), 9.40 (1H, d, J=8 Hz, —CONH—)

(b)

7β-[2-(2-Aminothiazol-4-yl)-(Z)-2-isopropoxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-isopropoxyiminoacetamido]-3-[(1-amino-1H-tetrazol-5-yl)thiomethyl]-3-cephem-4-carboxylic acid (2.90 g, 3.7 mmol) in 80% formic acid (12 ml) was treated in a manner similar to that described in Example 6, (d) to give pale brown powder of 7β-[2-(2-aminothiazol-4-yl)-(Z)-2-isopropoxyiminoacetamido]-3-[(1-amino-1H-tetrazol-5-yl)thiomethyl]-3-cephem-4-carboxylic acid (0.83 g, 41.5%).

IR$\nu_{max}^{Nujol}$ (cm$^{-1}$): 3320, 3200, 1775, 1675, 1115, 1000

NMR(DMSO-d$_6$)ppm: 1.20 (6H, d, J=6 Hz, CH(CH$_3$)$_2$, 5.10 (1H, d J=5 Hz, H at 6th position), 5.5–5.9 (1H, m, H at 7th position), 6.65 (1H, s, H at 5th position of thiazole), 9.45 (1H, d, J=8 Hz, —CONH—)

The acid was converted into the sodium salt according to the procedure described in Example 6, (d) to give pale yellow powder.

IR$\nu_{max}^{Nujol}$ (cm$^{-1}$): 3300, 1765, 1660, 1610, 1540, 1020, 990

NMR(DMSO-d$_6$)ppm: 1.20 (6H, d, J=6 Hz, —CH(CH$_3$)$_2$), 4.30 (2H, broad, CH$_2$ at C$^{3'}$), 5.00 (1H, d, J=5 Hz, H at 6th position), 5.65 (1H, m, H at 7th position), 6.70 (1H, s, H at 5th position of thiazole), 6.90 (2H, broad, s, N—NH$_2$), 7.20 (2H, broad, C—NH$_2$), 9.40 (1H, d, J=8 Hz, —CONH—)

EXAMPLE 23

7β-[2-(2-Aminothiazol-4-yl)-(Z)-2-cyclopentyloxyiminoacetamido]-3-[(1-amino-1H-tetrazol-5-yl)thiomethyl]-3-cephem-4-carboxylic acid (a)

7β-[2-(2-Tritylaminothiazol-4-yl)-(Z)-2-cyclopentyloxyiminoacetamido]-3-[(1-amino-1H-tetrazol-5-yl)thiomethyl]-3-cephem-4-carboxylic acid A solution of 2-(2-tritylaminothiazol-4-yl)-(Z)-2-cyclopentyloxyiminoacetic acid (3.23 g, 6.5 mmol), 1-hydroxybenzotriazole (1.01 g, 7.47 mmol) and N,N'-dicyclohexylcarbodiimide (1.47 g, 7.15 mmol) in dimethylacetamide (36 ml) was stirred at room temperature for 2.5 hours. To the solution was added a solution of 7β-amino-3-[(1-amino-1H-tetrazol-5-yl)thiomethyl]-3-cephem-4-carboxylic acid (2.35 g, 7.15 mmol) and triethylamine (1.44 g, 13 mmol) in dimethylacetamide (18 ml) and water (2.4 ml) and the mixture was stirred at room temperature for 17 hours. Then the mixture was treated in a manner to that described in Example 6, (c) to give pale brown powder of 7β-[2-(2-tritylaminothiazol-4-yl)-(Z)-2-cyclopentyloxyiminoacetamido]-3-[(1-amino-1H-tetrazol-5-yl)thiomethyl]-3-cephem-4-carboxylic acid (2.67 g, 51%).

IR$\nu_{max}^{Nujol}$ (cm$^{-1}$): 3300, 1780, 1670, 1590, 1510, 1100, 990

NMR(DMSO-d$_6$)ppm: 1.3–1.9 (8H, m, —(CH$_2$)$_4$—), 3.65 (2H, broad, CH$_2$ at 3rd position), 4.25 (2H, broad, H at C$^{3'}$), 4.60 (1H, broad, —OCH), 5.10 (1H, d, H=5 Hz, H at 6th position), 5.4–5.8 (1H, m, H at 7th position), 6.65 (1H, s, H at 5th position of thiazole ring), 6.95–7.5 (18H, NH, NH$_2$ and H on benzene ring), 9.40 (1H, d, J=8 Hz, —CONH—)

(b)

7β-[2-(2-Aminothiazol-4-yl)-(Z)-2-cyclopentyloxyiminoacetamido]-3-[(1-amino-1H-tetrazol-5-yl)thiomethyl]-3-cephem-4-carboxylic acid A solution of 7β-[2-(2-tritylaminothiazol-4-yl)-(Z)-2-cyclopentyloxyiminoacetamido]-3-[(1-amino-1H-tetrazol-5-yl)thiomethyl]-3-cephem-4-carboxylic acid (2.27 g, 2.8 mmol) in 80% formic acid (11 ml) was stirred at room temperature for 50 minutes and then treated in a manner similar to that described in Example 6, (d) to give pale brown powder of 7β-[2-(2-aminothiazol-4-yl)-(Z)-2-cyclopentyloxyiminoacetamido]-3-[(1-amino-1H-tetrazol-5-yl)thiomethyl]-3-cephem-4-carboxylic acid (0.53 g, 33%).

IR$\nu_{max}^{Nujol}$ (cm$^{-1}$): 3275, 3175, 1770, 1660, 1620, 1520, 1100, 990

Rf: 0.53 (SiO$_2$, n-butanol:acetic acid:water=4:1:2)

NMR(DMSO-d$_6$)ppm: 1.3–2.0 (8H, m, —(CH$_2$)$_4$—), 3.65 (2H, broad, CH$_2$ at 3rd position), 4.30 (2H, broad, CH$_2$ at C$^{3'}$ position), 4.60 (1H, broad, —OCH), 5.10 (1H, broad, H at 6th position), 5.4–5.9 (1H, m, H at 7th position), 6.65 (1H, s, H at 5th position of thiazole), 6.75–7.35 (4H, m, NH$_2$×2), 9.45 (1H, broad, —CONH—)

EXAMPLE 24

7β-[2-(2-Aminothiazol-4-yl)-(Z)-2-(1-carboxycyclopentyloxyimino)acetamido]-3-[(1-amino-1H-tetrazol-5-yl)thiomethyl]-3-cephem-4-carboxylic acid (a)

7β-[2-(2-Tritylamiothiazol-4-yl)-(Z)-2-(1-tert-butoxycarbonylcyclopentyloxyimino)acetamido]-3-[(1-amino-1H-tetrazol-5-yl)thiomethyl]-3-cephem-4-carboxylic acid A solution of 2-(2-tritylaminothiazol-4-yl)-(Z)-2-(1-tert-butoxycarbonylcyclopentyloxyimino)acetic acid (2.80 g, 4.7 mmol), 1-hydroxybenzotriazole (0.73 g, 5.4 mmol) and N,N'-dicyclohexylcarbodiimide (1.07 g, 5.17 mmol) in dimethylacetamide (26 ml) was stirred at room temperature for 2.5 hours. To the solution was added a solution of 7β-amino-3-[(1-amino-1H-tetrazol-5-yl)thiomethyl]-3-cephem-4-carboxylic acid (1.70 g, 5.17 mmol) and triethylamine (1.05 g, 10.3 mmol) in dimethylacetamide (13 ml) and water (1.7 ml), and the mixture was stirred at room temperature for 17 hours. The mixture was acidified with citric acid to pH 3.5 and extracted with ethyl acetate. The extract was washed with water, dried over magnesium sulfate, and evaporated. The residue was treated with isopropyl ether to give pale brown powder of 7β-[2-(2-tritylaminothiazol-4-yl)-(Z)-2-(1-tert-butoxycarbonylcyclopentyloxyimino)acetamido]-3-[(1-amino-1H-tetrazol-5-yl)thiomethyl]-3-cephem-4-carboxylic acid (3.3 g).

IR $\lambda_{max}^{Nujol}$ (cm$^{-1}$): 3300, 2800–2300, 1780, 1710, 1680, 1620, 1520, 1150, 990

Rf: 0.42 (SiO$_2$, chloroform:ethyl acetate:methanol:acetic acid=5:5:1:1)

NMR(DMSO-d$_6$)ppm: 1.35 (9H, s, CH$_3\times$3), 1.5–2.3 (8H, m, —(CH$_2$)$_4$—), 3.65 (2H, broad, CH$_2$ at 2nd position), 4.20 (2H, broad, CH$_2$ at C$^{3'}$), 5.10 (1H, d, J=4 Hz H at 6th position), 5.60 (1H, m, H at 7th position), 6.70 (1H, broad, H at 5th position of thiazole), 7.0 (2H, broad, NH$_2$), 8.75 (1H, broad, NH), 9.25 (1H, d, J=8 Hz, —CONH—)

(b)

7β-[2-(2-Aminothiazol-4-yl)-(Z)-2-(1-carboxycylopentoxyimino)acetamido]-3-[(1-amino-1H-tetrazol-5-yl)thiomethyl]-3-cephem-4-carboxylic acid A solution of 7β-[2-(2-tritylaminothiazol-4-yl)-(Z)-2-(1-tert-butoxycarbonylcyclopentoxyimino)acetamido]-3-[(1-amino-1H-tetrazol-5-yl)thiomethyl]-3-cephem-4-carboxylic acid (crude, 3.0 g) in 80% formic acid (12 ml) was stirred at room temperature for an hour and then treated with trifluoroacetic acid in a manner similar to that described in Example 16, (b) to give pale yellow powder of 7β-[2-(2-aminothiazol-4-yl)-(Z)-2-(1-carboxycyclopentoxyimino)acetamido]-3-[(1-amino-1H-tetrazol-5-yl)thiomethyl]-3-cephem-4-carboxylic acid disodium salt [0.29 g, 9.5% from 2-(2-tritylaminothiazol-4-yl)-(Z)-2-(1-tert-butoxycarbonylcyclopentyloxyimino)-acetic acid].

IR$\nu_{max}^{Nujol}$ (cm$^{-1}$): 3300, 1750, 1650, 1650, 1580, 1520, 980

Rf: 0.44 (SiO$_2$, n-butanol:acetic acid:water=4:1:2)

NMR(DMSO-d$_6$)ppm: 1.5–2.3 (8H, broad, —(CH$_2$)$_4$—), 4.40 (2H, broad, CH$_2$ at C$^{3'}$), 5.00 (1H, d, J=5 Hz, H at 6th position), 5.70 (1H, m, H at 7th position), 6.75 (1H, s, H at 5th position of thiazole), 6.90 (2H, broad, —N—NH$_2$), 7.20 (2H, broad, —C—NH$_2$), 11.25 (1H, d, J=8 Hz, —CONH—)

What is claimed is:

1. A cephalosporin compound selected from the group consisting of a (Z) isomer of a compound of the formula:

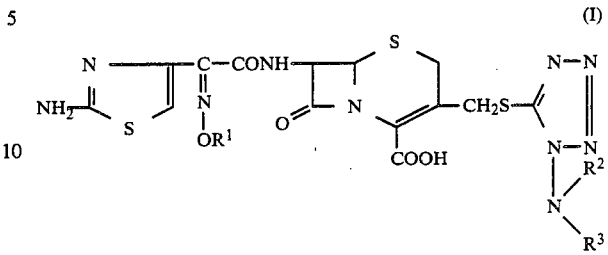

(I)

wherein R$^1$ is methyl or tetrazolylmethyl and R$^2$ and R$^3$ are a hydrogen atom, or a pharmaceutically acceptable salt thereof.

2. The cephalosporin compound of claim 1, which is 7β-[2-(2-aminothiazol-4-yl)-(Z)-2-methoxyiminoacetamido]-3-[(1-amino-1H-tetrazol-5-yl)thiomethyl]-3-cephem-4-carboxylic acid or a pharmaceutically acceptable salt thereof.

3. The cephalosporin compound of claim 1, which is 7β-[2-(2-aminothiazol-4-yl)-(Z)-2-(tetrazol-5-yl-methoxyimino)acetamido]-3-[(1-amino-1H-tetrazol-5-yl)thiomethyl]-3-cephem-4-carboxylic acid or a pharmaceutically acceptable salt thereof.

4. An antibacterial composition comprising an effective antibacterial amount of the cephalosporin compound selected from the group consisting of a (Z) isomer of a compound of the formula:

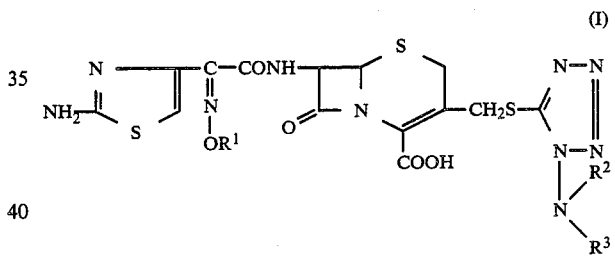

(I)

wherein R$^1$ is methyl or tetrazolylmethyl and R$^2$ and R$^3$ are a hydrogen atom, or a pharmaceutically acceptable salt thereof and a pharmaceutically acceptable carrier therefor.

5. A method of treating an infectious disease caused by gram-positive or gram-negative bacteria in animals or humans which comprises administering thereto an effective antibaterial amount of the cephalosporin compound selected from the group consisting of a (Z) isomer of a compound of the formula:

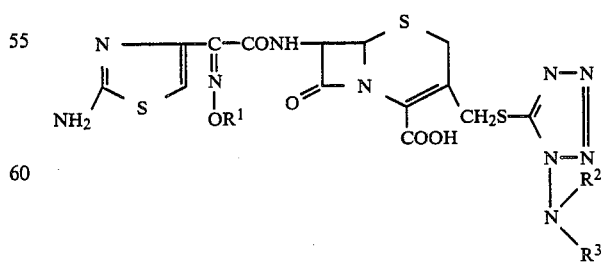

wherein R$^1$ is methyl or tetrazolylmethyl and R$^2$ and R$^3$ are hydrogen atom, or a pharmaceutically acceptable salt thereof.

* * * * *